US012710688B2

(12) United States Patent
Atiya et al.

(10) Patent No.: US 12,710,688 B2
(45) Date of Patent: Aug. 18, 2026

(54) ULTRAMINIATURE PATTERN PROJECTOR

(71) Applicant: Align Technology, Inc., San Jose, CA (US)

(72) Inventors: Yossef Atiya, Modiin-Maccabim-Reut (IL); Ofer Saphier, Rechovot (IL); Noam Shekel, Kiryat Gat (IL)

(73) Assignee: Align Technology, Inc., San Jose, CA (US)

( * ) Notice: Subject to any disclaimer, the term of this patent is extended or adjusted under 35 U.S.C. 154(b) by 364 days.

(21) Appl. No.: 18/226,651

(22) Filed: Jul. 26, 2023

(65) Prior Publication Data

US 2024/0036448 A1 Feb. 1, 2024

Related U.S. Application Data

(60) Provisional application No. 63/411,555, filed on Sep. 29, 2022, provisional application No. 63/369,642, filed on Jul. 27, 2022.

(51) Int. Cl.
*G03B 21/14* (2006.01)
*A61B 1/00* (2006.01)
(Continued)

(52) U.S. Cl.
CPC ........ *G03B 21/145* (2013.01); *A61B 1/00096* (2013.01); *A61C 9/006* (2013.01);
(Continued)

(58) Field of Classification Search
CPC ...... G03B 21/145; G03B 17/54; G03B 21/16; G03B 21/2013; G03B 21/2033;
(Continued)

(56) References Cited

U.S. PATENT DOCUMENTS 6,099,314 A 8/2000 Kopelman et al.
6,334,772 B1 1/2002 Taub et al.
(Continued)

FOREIGN PATENT DOCUMENTS

WO 2020264035 A1 12/2020

OTHER PUBLICATIONS

Co-pending U.S. Appl. No. 29/768,525, inventors Zakhar; Ginzburg et al., filed Jan. 29, 2021.
(Continued)

*Primary Examiner* — Michael Lee
(74) *Attorney, Agent, or Firm* — Lowenstein Sandler LLP

(57) ABSTRACT

An apparatus for intraoral scanning comprises an elongate wand comprising a probe at a distal end of the elongate wand. The apparatus further comprises one or more structured light projectors disposed within the probe, each structured light projector comprising: (a) a housing; (b) a light source disposed within the housing and comprising: a semiconductor laser die; and a beam shaping optical element; and (c) a pattern generating optical element. A distance D between an emission point of the semiconductor laser die and an input face of the beam shaping optical element is 50-250 microns. Each structured light projector is configured to project a pattern of light onto an intraoral surface when the light source of the structured light projector is activated to emit light through the pattern generating optical element of the structured light projector.

24 Claims, 18 Drawing Sheets

(51) Int. Cl.
*A61C 9/00* (2006.01)
*G03B 17/54* (2021.01)
*G03B 21/16* (2006.01)
*G03B 21/20* (2006.01)

(52) U.S. Cl.
CPC ............. *G03B 17/54* (2013.01); *G03B 21/16* (2013.01); *G03B 21/2013* (2013.01); *G03B 21/2033* (2013.01); *G03B 21/2066* (2013.01); *G03B 21/208* (2013.01)

(58) Field of Classification Search
CPC .............. G03B 21/2066; G03B 21/208; A61B 1/00096; A61B 1/00194; A61B 1/0605; A61B 1/0676; A61C 9/006; A61C 9/0053
See application file for complete search history.

(56) References Cited

U.S. PATENT DOCUMENTS

| | | | |
|---|---|---|---|
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,845,175 | B2 | 1/2005 | Kopelman et al. |
| 6,979,196 | B2 | 12/2005 | Nikolskiy et al. |
| 7,030,383 | B2 | 4/2006 | Babayoff et al. |
| 7,202,466 | B2 | 4/2007 | Babayoff et al. |
| 7,255,558 | B2 | 8/2007 | Babayoff et al. |
| 7,286,954 | B2 | 10/2007 | Kopelman et al. |
| 7,319,529 | B2 | 1/2008 | Babayoff |
| 7,373,286 | B2 | 5/2008 | Nikolskiy et al. |
| 7,507,088 | B2 | 3/2009 | Taub et al. |
| 7,545,372 | B2 | 6/2009 | Kopelman et al. |
| 7,698,068 | B2 | 4/2010 | Babayoff |
| 7,872,760 | B2 | 1/2011 | Ertl |
| 7,916,911 | B2 | 3/2011 | Kaza et al. |
| 8,108,189 | B2 | 1/2012 | Chelnokov et al. |
| 8,244,028 | B2 | 8/2012 | Kuo et al. |
| 8,587,582 | B2 | 11/2013 | Matov et al. |
| 8,948,482 | B2 | 2/2015 | Levin |
| D742,518 | S | 11/2015 | Barak et al. |
| 9,192,305 | B2 | 11/2015 | Levin |
| 9,261,356 | B2 | 2/2016 | Lampert et al. |
| 9,261,358 | B2 | 2/2016 | Atiya et al. |
| 9,299,192 | B2 | 3/2016 | Kopelman |
| D760,901 | S | 7/2016 | Barak et al. |
| 9,393,087 | B2 | 7/2016 | Moalem |
| 9,408,679 | B2 | 8/2016 | Kopelman |
| 9,431,887 | B2 | 8/2016 | Boltanski |
| 9,439,568 | B2 | 9/2016 | Atiya et al. |
| 9,451,873 | B1 | 9/2016 | Kopelman et al. |
| D768,861 | S | 10/2016 | Barak et al. |
| D771,817 | S | 11/2016 | Barak et al. |
| 9,491,863 | B2 | 11/2016 | Boltanski |
| D774,193 | S | 12/2016 | Makmel et al. |
| 9,510,757 | B2 | 12/2016 | Kopelman et al. |
| 9,660,418 | B2 | 5/2017 | Atiya et al. |
| 9,668,829 | B2 | 6/2017 | Kopelman |
| 9,675,430 | B2 | 6/2017 | Verker et al. |
| 9,693,839 | B2 | 7/2017 | Atiya et al. |
| 9,717,402 | B2 | 8/2017 | Lampert et al. |
| 9,724,177 | B2 | 8/2017 | Levin |
| 9,844,426 | B2 | 12/2017 | Atiya et al. |
| 10,076,389 | B2 | 9/2018 | Wu et al. |
| 10,098,714 | B2 | 10/2018 | Kuo |
| 10,108,269 | B2 | 10/2018 | Sabina et al. |
| 10,111,581 | B2 | 10/2018 | Makmel |
| 10,111,714 | B2 | 10/2018 | Kopelman et al. |
| 10,123,706 | B2 | 11/2018 | Elbaz et al. |
| 10,136,972 | B2 | 11/2018 | Sabina et al. |
| 10,380,212 | B2 | 8/2019 | Elbaz et al. |
| 10,390,913 | B2 | 8/2019 | Sabina et al. |
| 10,453,269 | B2 | 10/2019 | Furst |
| 10,456,043 | B2 | 10/2019 | Atiya et al. |
| 10,499,793 | B2 | 12/2019 | Ozerov et al. |
| 10,504,386 | B2 | 12/2019 | Levin et al. |
| 10,507,087 | B2 | 12/2019 | Elbaz et al. |
| 10,517,482 | B2 | 12/2019 | Sato et al. |
| 10,695,150 | B2 | 6/2020 | Kopelman et al. |
| 10,708,574 | B2 | 7/2020 | Furst et al. |
| 10,772,506 | B2 | 9/2020 | Atiya et al. |
| 10,813,727 | B2 | 10/2020 | Sabina et al. |
| 10,888,399 | B2 | 1/2021 | Kopelman et al. |
| 10,952,816 | B2 | 3/2021 | Kopelman |
| 10,980,613 | B2 | 4/2021 | Shanjani et al. |
| 11,013,581 | B2 | 5/2021 | Sabina et al. |
| D925,739 | S | 7/2021 | Shalev et al. |
| 11,238,586 | B2 | 2/2022 | Minchenkov et al. |
| 11,367,192 | B2 | 6/2022 | Kopelman et al. |
| 11,455,727 | B2 | 9/2022 | Minchenkov et al. |
| 11,478,132 | B2 | 10/2022 | Kopelman et al. |
| 11,633,268 | B2 | 4/2023 | Moalem et al. |
| 11,707,238 | B2 | 7/2023 | Moshe et al. |
| RE49,605 | E | 8/2023 | Kopelman |
| 11,744,681 | B2 | 9/2023 | Kopelman et al. |
| 11,759,277 | B2 | 9/2023 | Shalev et al. |
| 2014/0272764 | A1* | 9/2014 | Miller .................... A61B 1/051 433/29 |
| 2014/0302452 | A1* | 10/2014 | Hack .................. A61B 1/00193 433/29 |
| 2019/0388193 | A1* | 12/2019 | Saphier ................... G06T 17/00 |
| 2019/0388194 | A1 | 12/2019 | Atiya et al. |
| 2020/0404243 | A1 | 12/2020 | Saphier et al. |
| 2021/0059796 | A1 | 3/2021 | Weiss et al. |
| 2021/0121049 | A1 | 4/2021 | Rudnitsky et al. |
| 2021/0128281 | A1 | 5/2021 | Peleg |
| 2021/0137653 | A1 | 5/2021 | Saphier et al. |
| 2021/0196152 | A1 | 7/2021 | Saphier et al. |

OTHER PUBLICATIONS

Co-pending U.S. Appl. No. 29/768,563, inventors Zakhar; Ginzburg et al., filed Jan. 29, 2021.

U.S. Reissue U.S. Appl. No. 16/784,515, inventor Babayoff, Noam, filed Feb. 7, 2020.

U.S. Reissue U.S. Appl. No. 16/784,501, inventor Babayoff, Noam, filed Feb. 7, 2020.

U.S. Reissue U.S. Appl. No. 16/784,493, inventor Babayoff, Noam, filed Feb. 7, 2020.

* cited by examiner

SIDE VIEW

TOP VIEW

SIDE VIEW

ULTRAMINIATURE PATTERN PROJECTOR

RELATED APPLICATIONS

This application claims the benefit under 35 U.S.C. § 119(e) of U.S. Provisional Application No. 63/369,642, filed Jul. 27, 2022, and further claims the benefit under 35 U.S.C. § 119(e) of the of U.S. Provisional Application No. 63/411,555, filed Sep. 29, 2022, both of which are hereby incorporated by reference.

FIELD OF THE INVENTION

The present invention relates generally to three-dimensional imaging, and more particularly to intraoral three-dimensional imaging using structured light illumination.

BACKGROUND

Dental impressions of a subject's intraoral three-dimensional surface, e.g., teeth and gingiva, are used for planning dental procedures. Traditional dental impressions are made using a dental impression tray filled with an impression material, e.g., PVS or alginate, into which the subject bites. The impression material then solidifies into a negative imprint of the teeth and gingiva, from which a three-dimensional model of the teeth and gingiva can be formed.

Digital dental impressions utilize intraoral scanning to generate three-dimensional digital models of an intraoral three-dimensional surface of a subject. Digital intraoral scanners often use structured light three-dimensional imaging. The surface of a subject's teeth may be highly reflective and somewhat translucent, which may reduce the contrast in the structured light pattern reflecting off the teeth. Therefore, in order to improve the capture of an intraoral scan, when using a digital intraoral scanner that utilizes structured light three-dimensional imaging, a subject's teeth may be coated with an opaque powder prior to scanning in order to facilitate a usable level of contrast of the structured light pattern, e.g., in order to turn the surface into a scattering surface. While intraoral scanners utilizing structured light three-dimensional imaging have made some progress, additional advantages may be had.

International Patent Application No. PCT/US2019/038510 to Saphier et al., which published as WO 2019/246542 to Saphier et al., is assigned to the assignee of the present application, and is incorporated herein by reference, describes an apparatus for intraoral scanning including an elongate handheld wand that has a probe. One or more light projectors and two or more cameras are disposed within the probe. The light projectors each have a pattern generating optical element, which may use diffraction or refraction to form a light pattern. Each camera may be configured to focus between 1 mm and 30 mm from a lens that is farthest from the camera sensor. Other applications are also described.

International Patent Application No. PCT/US2020/039438 to Saphier et al., which published as WO 2020/264035 to Saphier et al., is assigned to the assignee of the present application, and is incorporated herein by reference, describes a method for generating a 3D image, including driving structured light projector(s) to project a pattern of light on an intraoral 3D surface, and driving camera(s) to capture images, each image including at least a portion of the projected pattern, each one of the camera(s) comprising an array of pixels. A processor compares a series of images captured by each camera and determines which of the portions of the projected pattern can be tracked across the images. The processor constructs a three-dimensional model of the intraoral three-dimensional surface based at least in part on the comparison of the series of images. Other embodiments are also described.

SUMMARY OF THE INVENTION

Applications of the present invention include systems and methods related to a three-dimensional intraoral scanning device that includes one or more cameras, and one or more light projectors, e.g., structured light projectors. For example, certain applications of the present invention may be related to an intraoral scanning device having a plurality of cameras and a plurality of structured light projectors. For example, in some particular applications of the present invention, an apparatus is provided for intraoral scanning, the apparatus including an elongate handheld wand with a probe at the distal end of the handheld handle. Typically, the one or more structured light projectors are disposed within the probe.

In accordance with some applications of the present invention, each structured light projector includes a housing, within which is disposed a light source. In some embodiments the housing is a sealed housing (e.g., is hermetically sealed). Each light source includes at least one semiconductor laser die and at least one beam shaping optical element. Typically, the semiconductor laser die and the beam shaping optical element are disposed within a common chamber of the housing. The inventors have realized that placing the beam shaping optical element and the semiconductor laser die of the structured light projector within the same chamber of the housing enables a distance between an emission point of the semiconductor laser die and an input face of the beam shaping optical element to be shorter than conventional laser diodes permit. Typically, a distance D between an emission point of the semiconductor laser diode and an input face of the beam shaping optical element is at least 50 microns and/or less than 250 microns. This in turn results in a number of advantages, further described hereinbelow. Some examples of the advantages provided by applications of the present invention are:

- overall reduction in size of the structured light projector, in turn enabling a reduction in size of the probe as well as increased flexibility in the arrangement of the structured light projectors and the cameras,
- increased collection efficiency of the laser light,
- increased depth of focus of the structured light projector,
- use of multiple laser dies within a single structured light projector, increasing the quantity of structured light features used for 3D reconstruction without increasing the size of and/or number of structured light projectors, and
- reduced speckle noise when using multiple laser dies.

Each structured light projector includes at least one pattern generating optical element positioned such that each structured light projector projects a pattern of light onto an intraoral surface when the light source of the structured light projector is activated to emit light through the pattern generating optical element of the structured light projector.

There is therefore provided, in accordance with some applications of the present invention, a first apparatus for intraoral scanning, the first apparatus including:

an elongate handheld wand including a probe at a distal end of the handheld wand; and one or more structured light projectors disposed within the probe, each structured light projector including:

(a) a housing;

(b) a light source disposed within the housing and comprising:

a semiconductor laser die; and a beam shaping optical element; and (c) a pattern generating optical element, wherein:

a distance D between an emission point of the semiconductor laser die and an input face of the beam shaping optical element is 50-250 microns, and each structured light projector is configured to project a pattern of light onto an intraoral surface when the light source of the structured light projector is activated to emit light through the pattern generating optical element of the structured light projector.

For some applications, the housing is a sealed housing.

For some applications, the semiconductor laser die and the beam shaping optical element being disposed within the housing (e.g., within the sealed housing) and distance D being 50-250 microns together allow a longest dimension of the sealed housing to be 1.5-2.5 mm.

For some applications, a height of the housing is 1.6-2.4 mm.

For some applications, the beam shaping optical element is positioned within the housing such that at least 75% of the light emitted by the semiconductor laser die enters the beam shaping optical element.

For some applications, the beam shaping optical element is positioned within the housing such that 80-90% of the light emitted by the semiconductor laser die enters the beam shaping optical element.

For some applications, the housing includes metal and the semiconductor laser die is disposed within the housing such that heat is conducted from the semiconductor laser die to the metal of the housing.

For some applications, the semiconductor laser die is mounted on a submount within the housing such that heat is conducted from the semiconductor laser die to the metal of the housing through the submount.

For some applications, the submount is ceramic.

For some applications, the apparatus further includes one or more cameras disposed within the probe, wherein a distance between (i) an optical axis of at least one camera and (ii) an optical axis of at least one structured light projector that is adjacent the at least one camera is 3-5 mm.

For some applications, (a) the probe includes a transparent window through which the one or more structured light projectors project light and through which the one or more cameras receive light, and (b) a distance from the transparent window at which 50% of the respective fields of view of the at least one camera and the at least one adjacent structured light projector overlap is 2-6 mm.

For some applications, (a) the probe includes a transparent window through which the one or more structured light projectors project light and through which the one or more cameras receive light, and (b) a distance from the transparent window at which the respective fields of view of the at least one camera and the at least one adjacent structured light projector start to overlap is 1-3 mm.

For some applications, the housing includes a transparent window through which the laser light exits the housing, and the transparent window includes the pattern generating optical element.

For some applications:

a. an angle between an optical axis of the beam shaping optical element and an optical axis of the pattern generating optical element is 65-120 degrees, and the apparatus further includes a mirror disposed within the housing and positioned so as to reflect the laser light exiting the beam shaping optical element toward the pattern generating optical element.

For some applications, the pattern generating optical element is disposed within the probe outside of the housing, and a distance the laser light travels from exiting the beam shaping optical element to entering the pattern generating optical element is 2-8 mm.

For some applications, the pattern generating optical element is disposed within the probe outside of the housing, and a distance the laser light travels from exiting the beam shaping optical element to entering the pattern generating optical element is 8-25 mm.

For some applications:

a. the pattern generating optical element is disposed within the probe outside of the housing such that an angle between an optical axis of the beam shaping optical element and an optical axis of the pattern generating optical element is 50-100 degrees, b. the apparatus further includes a mirror disposed within the probe and positioned so as to reflect the laser light exiting the beam shaping optical element toward the pattern generating optical element, and c. a distance the laser light travels from exiting the beam shaping optical element to entering the pattern generating optical element is 8-25 mm.

For some applications, for at least one of the one or more structured light projectors the semiconductor laser die is a first semiconductor laser die and the light source further includes a second semiconductor laser die.

For some applications, the first and second semiconductor laser dies are mounted on a common submount within the housing.

For some applications, the first and second semiconductor laser dies having different wavelengths, and the apparatus further includes a computer processor configured to activate the first and second semiconductor laser dies such that the at least one structured light projector projects a pattern in each of the two different wavelengths.

For some applications, the computer processor is configured to alternatingly activate the first and second semiconductor laser dies such that the at least one structured light projector alternatingly projects a pattern in each of the two different wavelengths.

For some applications, the computer processor is configured to concurrently activate the first and second semiconductor laser dies such that the at least one structured light projector concurrently projects a pattern in each of the two different wavelengths.

For some applications, the beam shaping optical element is a first beam shaping optical element and the light source further includes a second beam shaping optical element, the first and second beam shaping optical elements arranged such that laser light from the first semiconductor laser die enters and subsequently exits the first beam shaping optical element and laser light from the second semiconductor laser die enters and subsequently exits the second beam shaping optical element, and a. the pattern generating optical element is a first pattern generating optical element and the at least one structured light projector further includes a second pattern generating optical element, the first and second pattern generating optical elements arranged such that the laser light exiting the first beam shaping optical element enters the first pattern generating optical element and the laser light exiting the second beam shaping optical element enters the second pattern generating optical element.

For some applications, the first and second pattern generating optical elements project the same pattern of light, such that the at least one structured light projector projects (a) the pattern of light in the first wavelength in a first position onto the intraoral surface and (b) the pattern of light in the second wavelength translationally shifted with respect to the first position onto the intraoral surface.

For some applications, the projected pattern of light in the second wavelength is translationally shifted with respect to the first position by the distance between the optical axes of the first and second pattern generating optical elements.

For some applications, the at least one structured light projector projects a first pattern from the first pattern generating optical element and a second pattern from the second pattern generating optical element, the first pattern different from the second pattern.

For some applications, the first and second semiconductor laser dies are mounted within the housing such that the first and second semiconductor laser dies emit laser light in the same direction, and the first and second pattern generating optical elements are respective first and second areas of a common lens.

For some applications, the first and second semiconductor laser dies are mounted within the housing such that the first and second semiconductor laser dies emit laser light in the same direction, and the first and second beam shaping optical elements are respective first and second areas of a common lens.

For some applications, the first beam shaping optical element includes a first lens and the second beam shaping optical element includes a second lens, the first lens separate from the second lens.

For some applications, the beam shaping optical element is arranged such that laser light from each of the first and second semiconductor laser dies (i) enters the beam shaping element along different respective axes of the beam shaping optical element, and (ii) subsequently impinges on the pattern generating optical element at different respective angles, such that the projected pattern in each wavelength is angularly shifted about an optical axis of the pattern generating optical element.

For some applications, the first and second semiconductor laser dies having the same wavelength, and a. the apparatus further includes a computer processor configured to alternatingly activate the first and second semiconductor laser dies.

For some applications, the beam shaping optical element is a first beam shaping optical element and the light source further includes a second beam shaping optical element, the first and second beam shaping optical elements arranged such that laser light from the first semiconductor laser die enters and subsequently exits the first beam shaping optical element and laser light from the second semiconductor laser die enters and subsequently exits the second beam shaping optical element, and a. the pattern generating optical element is a first pattern generating optical element and the at least one structured light projector further includes a second pattern generating optical element, the first and second pattern generating optical elements arranged such that the laser light exiting the first beam shaping optical element enters the first pattern generating optical element and the laser light exiting the second beam shaping optical element enters the second pattern generating optical element.

For some applications, the first and second pattern generating optical elements project the same pattern of light, such that the at least one structured light projector alternatingly projects (a) the pattern of light in a first position onto the intraoral surface and (b) the pattern of light translationally shifted with respect to the first position onto the intraoral surface.

For some applications, the at least one structured light projector alternatingly projects a first pattern from the first pattern generating optical element and a second pattern from the second pattern generating optical element, the first pattern different from the second pattern.

For some applications, the first and second semiconductor laser dies are mounted within the housing such that the first and second semiconductor laser dies emit laser light in the same direction, and the first and second pattern generating optical elements are respective first and second areas of a common lens.

For some applications, the first and second semiconductor laser dies are mounted within the housing such that the first and second semiconductor laser dies emit laser light in the same direction, and the first and second beam shaping optical elements are respective first and second areas of a common lens.

For some applications, the first beam shaping optical element includes a first lens and the second beam shaping optical element includes a second lens, the first lens separate from the second lens.

For some applications:

a. the beam shaping optical element is arranged such that laser light from each of the first and second semiconductor laser dies (i) enters the beam shaping element along different respective axes of the beam shaping optical element, and (ii) subsequently impinges on the pattern generating optical element at different respective angles, such that the at least one structured light projector projects a pattern that is alternatingly angularly shifted about an optical axis of the pattern generating optical element.

For some applications, for at least one of the one or more structured light projectors:

a. the semiconductor laser die is a first semiconductor laser die and the light source further includes a second semiconductor laser die, the first and second semiconductor laser dies mounted within the housing such that the first and second semiconductor laser dies emit laser light in respective first and second directions, the first direction different from the second direction, and b. the apparatus further includes a computer processor configured to activate the first and second semiconductor laser dies such that the at least one structured light projector projects a first pattern in the first direction and a second pattern in the second direction.

For some applications, the first and second semiconductor laser dies are mounted on a common submount within the housing.

For some applications:

a. the beam shaping optical element is a first beam shaping optical element and the light source further includes a second beam shaping optical element, the first and second beam shaping optical elements arranged such that laser light from the first semiconductor laser die enters and subsequently exits the first beam shaping optical element and laser light from the second semiconductor laser die enters and subsequently exits the second beam shaping optical element, and b. the pattern generating optical element is a first pattern generating optical element and the at least one structured light projector further includes a second pattern generating optical element, the first and second pattern generating optical elements arranged such that the laser light exiting the first beam shaping optical element enters the first pattern generating optical element and the laser light exiting the second beam shaping optical element enters the second pattern generating optical element.

For some applications, the first and second semiconductor laser dies have the same wavelength.

For some applications, the first and second semiconductor laser dies have different wavelengths.

For some applications, the first direction and the second direction are opposite to each other.

For some applications, the computer processor is configured to activate the first and second semiconductor laser dies such that the at least one structured light projector alternatingly projects the first pattern in the first direction and the second pattern in the second direction.

For some applications, the computer processor is configured to activate the first and second semiconductor laser dies such that the at least one structured light projector projects, at the same time, the first pattern in the first direction and the second pattern in the second direction.

For some applications, for at least one of the one or more structured light projectors:

a. the pattern generating optical element is a first pattern generating optical element and the at least one structured light projector further includes a second pattern generating optical element, b. the first and second pattern generating optical elements are two respective areas on a common substrate that comprises a beam splitter and a reflector disposed within the substrate, and c. the apparatus further includes a computer processor configured to activate the semiconductor laser die such that:

d. laser light exiting the light source is split by the beam splitter into a first beam and a second beam within the substrate, and e. the first beam enters the first pattern generating optical element and the second beam is reflected by the reflector toward the second pattern generating optical element to yield two separate projected patterns that are translationally shifted with respect to each other.

For some applications, the first beam enters the first pattern generating optical element and the second beam is reflected by the reflector toward the second pattern generating optical element to yield two separate projected patterns that are shifted with respect to each other by the distance between the optical axes of the first and second pattern generating optical elements.

There is further provided, in accordance with some applications of the present invention, a second apparatus for intraoral scanning, the second apparatus including:

an elongate handheld wand including a probe at a distal end of the handheld wand; and one or more structured light projectors disposed within the probe, each structured light projector including:

(a) a housing;

(b) a light source disposed within the housing and comprising:

a semiconductor laser die; and a beam shaping optical element; and (c) a pattern generating optical element, wherein:

the semiconductor laser die and the beam shaping optical element are disposed within a common chamber of the housing, and each structured light projector is configured to project a pattern of light onto an intraoral surface when the light source of the structured light projector is activated to emit light through the pattern generating optical element of the structured light projector.

It is noted that all of the above-described applications of the first apparatus, may be performed with the second apparatus, mutatis mutandis.

The present invention will be more fully understood from the following detailed description of applications thereof, taken together with the drawings, in which:

DETAILED DESCRIPTION

Figure 1:
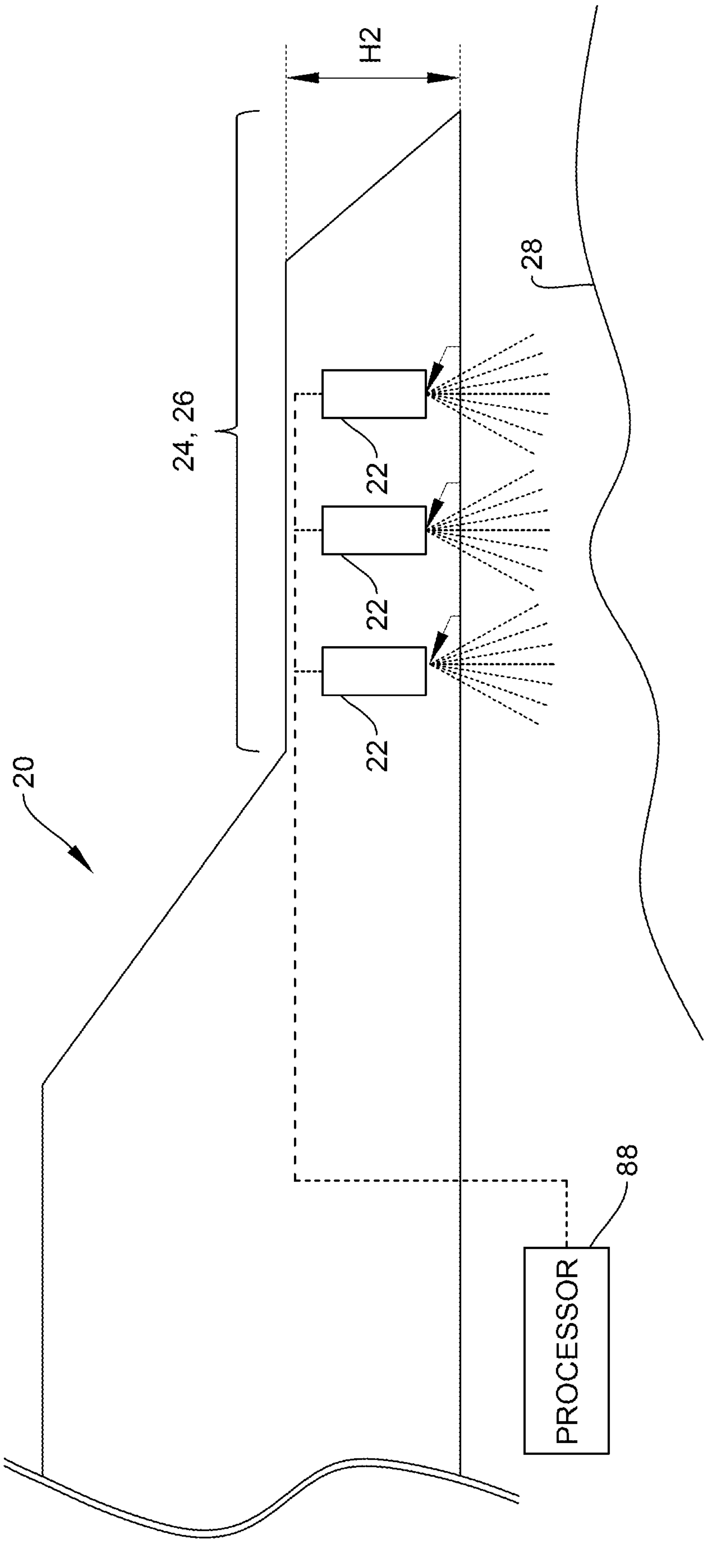
FIG. 1 is a schematic illustration of an elongate handheld wand for intraoral scanning, in accordance with some applications of the present invention.

Reference is now made to FIG. 1, which is a schematic illustration of an elongate handheld wand 20 for intraoral scanning, in accordance with some applications of the present invention. For some applications, elongate handheld wand 20 has a probe 24 at distal end 26 of handheld wand 20. One or more structured light projectors 22 are disposed within probe 24. It is noted that three structured light projectors 22 are shown in FIG. 1 by way of example and not limitation, and that the scope of the present invention includes one or more structured light projectors 22 disposed within probe 24. In some applications, during an intraoral scan, probe 24 enters an oral cavity of a subject in order to scan an intraoral surface 28.

Figure 2C:
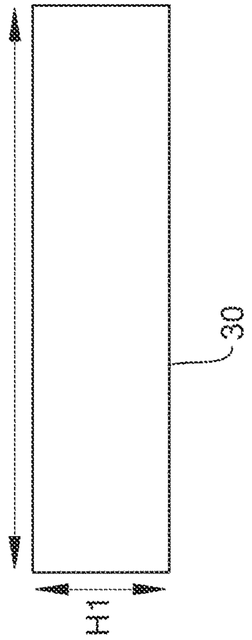
FIGS. 2A-C are schematic illustrations of a top view and two side views, respectively, of a structured light projector, in accordance with some applications of the present invention.
Figure 2A:
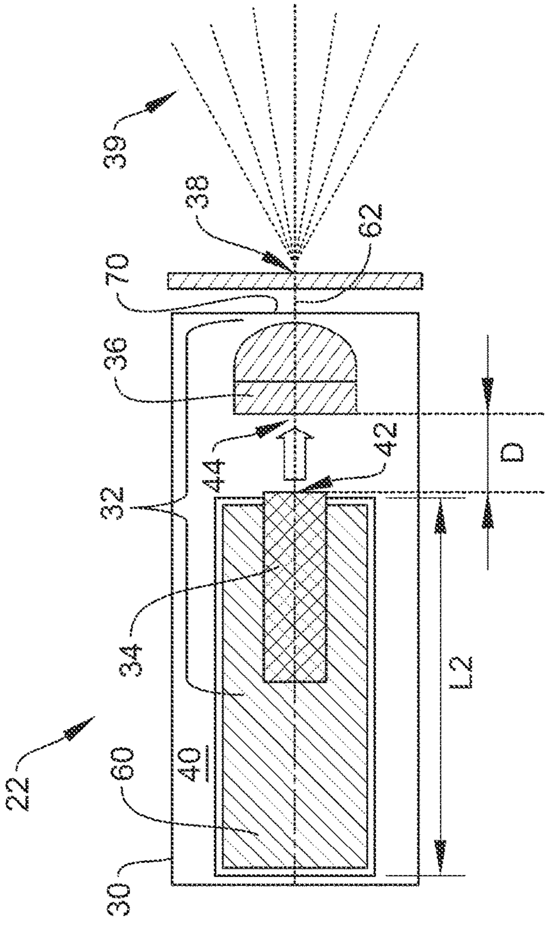
Figure 2B:
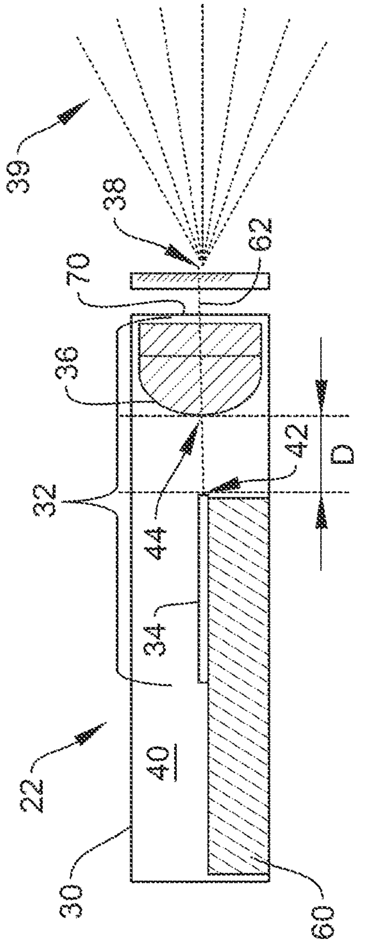

Reference is now made to FIGS. 2A-C, which are schematic illustrations of a top view and two side views, respectively, of a structured light projector 22, in accordance with some applications of the present invention. Each structured light projector 22 has a housing 30, e.g., a sealed housing such as a hermetically sealed housing, and a light source 32 disposed within sealed housing 30. In some embodiments, the sealed housing has an airtight seal. In some embodiments, the sealed housing does not have an airtight seal, but has a seal that prevents influx of liquid molecules. In some embodiments, the sealed housing is sealed against humidity and protects a laser die of structured light projector 22 against humidity. Embodiments are discussed below with reference to a sealed housing. However, it should be understood that embodiments may also include unsealed housings. Any discussion with reference to sealed housings also applies to embodiments in which the housings are not sealed.

Light source 32 includes a semiconductor laser die 34 and a beam shaping optical element 36. Semiconductor laser die 34 and beam shaping optical element 36 are typically disposed in a common chamber 40 of sealed housing 30, such that they are exposed to the same gas environment, i.e., there is fluid communication between semiconductor laser die 34 and beam shaping optical element 36. Positioning beam shaping optical element 36 within the same chamber 40 as semiconductor laser die 34 allows a distance D between an emission point 42 of semiconductor laser die 34 and an input face 44 of beam shaping optical element 36 to be smaller than conventional laser diodes (in which a beam shaping lens is positioned outside of the hermetically sealed housing of the diode) permit. For some applications, distance D is at least 50 microns and/or less than 250 microns. For some applications, (i) semiconductor laser die 34 and beam shaping optical element 36 both being disposed within sealed housing 30 and (ii) distance D being at least 50 microns and/or less than 250 microns together allow a longest dimension L1 (shown in FIG. 2C) of sealed housing 30 to be at least 1.5 mm and/or less than 2.5 mm. For some applications, a height H1 (shown in FIG. 2C) of sealed housing 30 is at least 1.6 mm and/or less than 2.4 mm. For some applications, sealed housing 30 is cylindrical and height H1 is a diameter of the cylinder. For some applications, sealed housing 30 is shaped as a prism, e.g., a rectangular prism.

Each structured light projector 22 also includes a pattern generating optical element 38, e.g., a diffractive optical element (DOE), or a refractive optical element. Each structured light projector 22 projects a pattern of light onto intraoral surface 28 when light source 32 of structured light projector 22 is activated to emit light 39 through pattern generating optical element 38 of structured light projector 22. For some applications, pattern generating optical element 38 is disposed within probe 24 but outside of sealed housing 30 of structured light projector 22, as is shown in FIGS. 2A-B.

Figure 3:
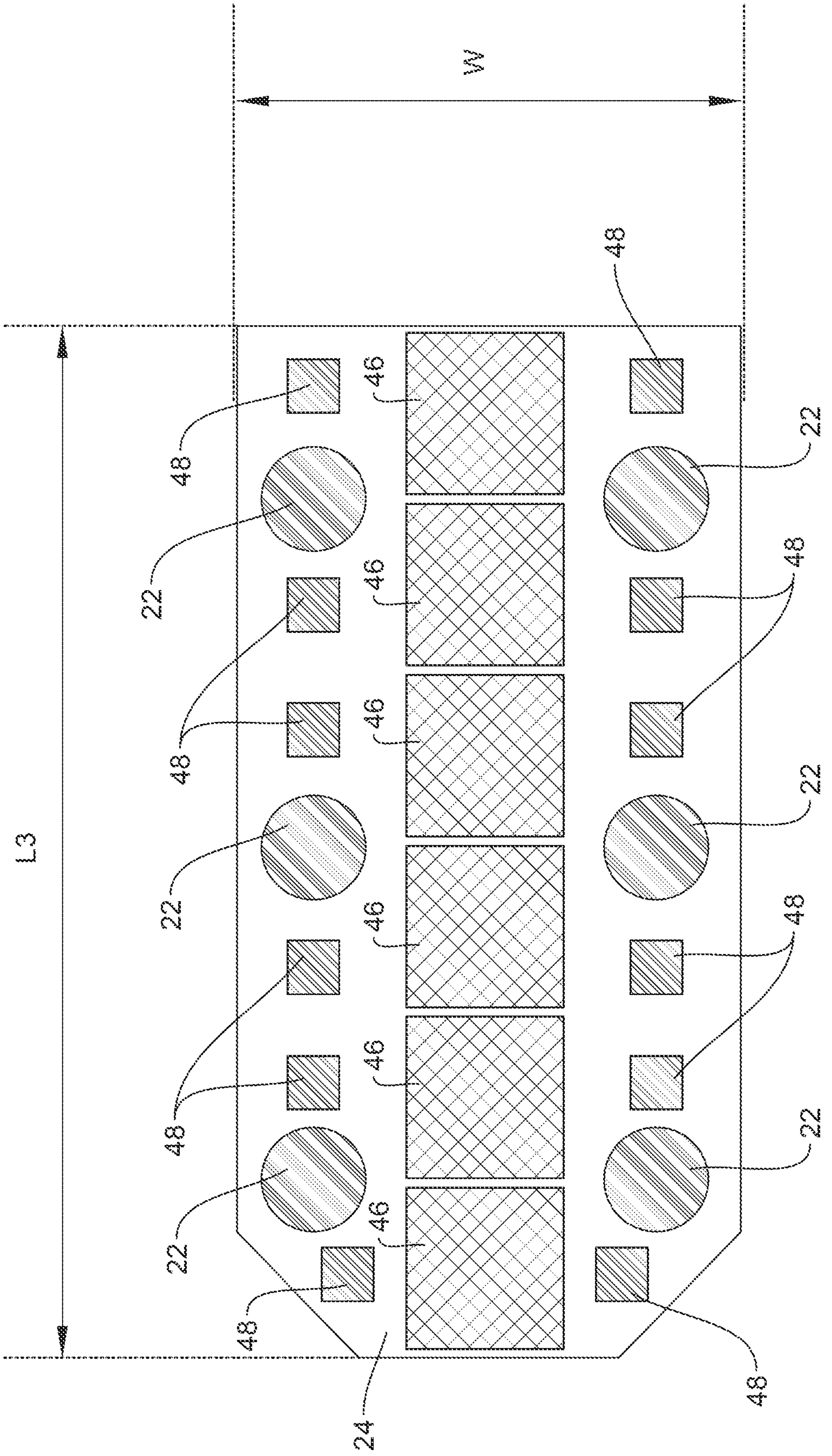
FIG. 3 is a schematic illustration of a probe of the elongate handheld wand showing an example configuration for positioning a plurality of structured light projectors and a plurality of cameras within the probe, in accordance with some applications of the present invention.

Reference is now made to FIG. 3, which is a schematic illustration of probe 24 showing an example configuration for positioning a plurality of structured light projectors 22 and a plurality of cameras 46 within probe 24, in accordance with some applications of the present invention. Broad-spectrum LED's 48 are shown as well, e.g., white light LED's or Near Infra-Red (NIR) LED's. The small dimensions described hereinabove of sealed housing 30, which includes beam shaping optical element 36 disposed within sealed housing 30, allow an overall reduction in size of probe 24. Typically, the reduction in size of probe 24 corresponds to the reduction in size of elements disposed within probe 24, i.e., the small size of structured light projector(s) 22 of these applications of the present invention allows a reduction in size of probe 24. Reducing the size of probe 24 may provide a more comfortable patient experience during an intraoral scan using elongate handheld wand 20. For some applications, a height H2 of probe 24 (shown in FIG. 1) is at least 10 mm and/or less than 15 mm, a width W of probe 24 (shown in FIG. 3) is at least 12 mm and/or less than 18 mm, and a length L3 (shown in FIG. 3) of probe 24 is at least 10 mm and/or less than 30 mm. Typically, a radio of width W to height H2 is at least 0.8 and/or less than 2.5. It is noted that the specific configuration shown in FIG. 3 and the specific number of structured light projectors 22, cameras 46, and broad-spectrum LED's 48 shown in FIG. 3 are by way of example only and are not limiting.

Figure 4:
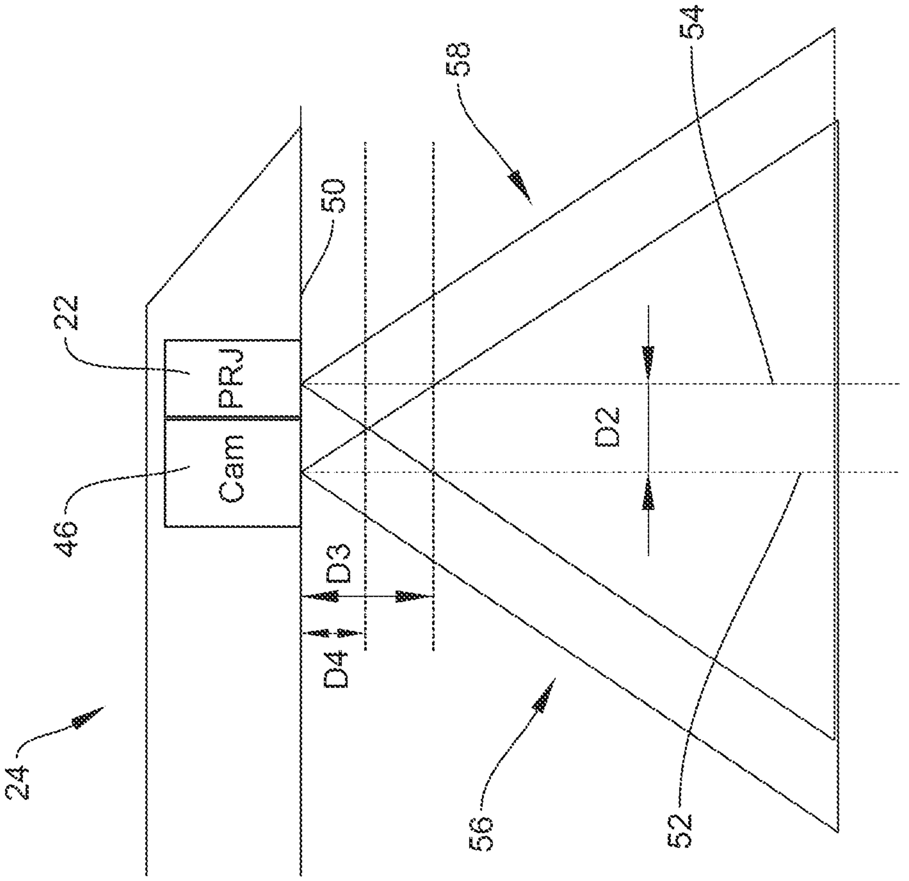
FIG. 4 is a schematic illustration of the probe showing a structured light projector disposed within the probe and a camera disposed within the probe, in accordance with some applications of the present invention.

Reference is now made to FIG. 4, which is a schematic illustration of probe 24 showing a structured light projector 22 disposed within probe 24, and a camera 46 disposed within probe 24, in accordance with some applications of the present invention. For some applications, one or more cameras 46 are disposed within the probe 24. Typically, probe 24 has a transparent window 50 through which one or more structured light projectors 22 project light and through which one or more cameras 46 receive light. The above-described small dimensions of sealed housing 30 of structured light projector 22 enable positioning structured light projectors 22 in close proximity to adjacent cameras 46. For example, in some applications, a distance D2 between (i) an optical axis 52 of at least one camera 46 and (ii) an optical axis 54 of at least one structured light projector 22 that is adjacent at least one camera 46 is at least 3 mm and/or less than 5 mm.

The close proximity between camera 46 and adjacent structured light projector 22 causes the respective fields of view 56 and 58 of camera 46 and adjacent structured light projector 22 to overlap each other at a close distance from transparent window 50. For some applications, a distance D3 from transparent window 50 at which 50% of the respective fields of view 56 and 58 of at least one camera 46 and at least one adjacent structured light projector 22 overlap is at least 2 mm and/or less than 6 mm. For some applications, a distance D4 from transparent window 50 at which respective fields of view 56 and 58 of at least one camera 46 and at least one adjacent structured light projector 22 start to overlap is at least 1 mm and/or less than 3 mm.

Figure 5B:
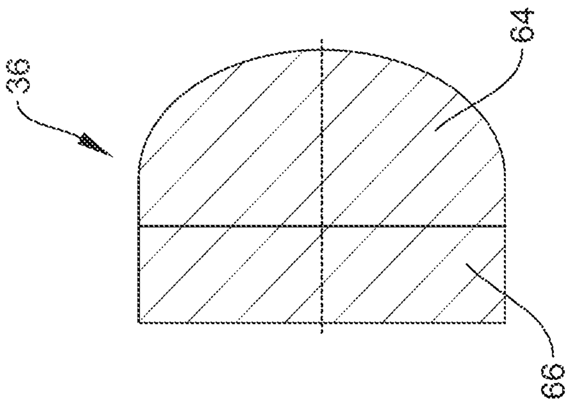
FIGS. 5A-B are schematic illustrations of the structured light projector and beam shaping optical element, in accordance with some applications of the present invention.
Figure 5A:
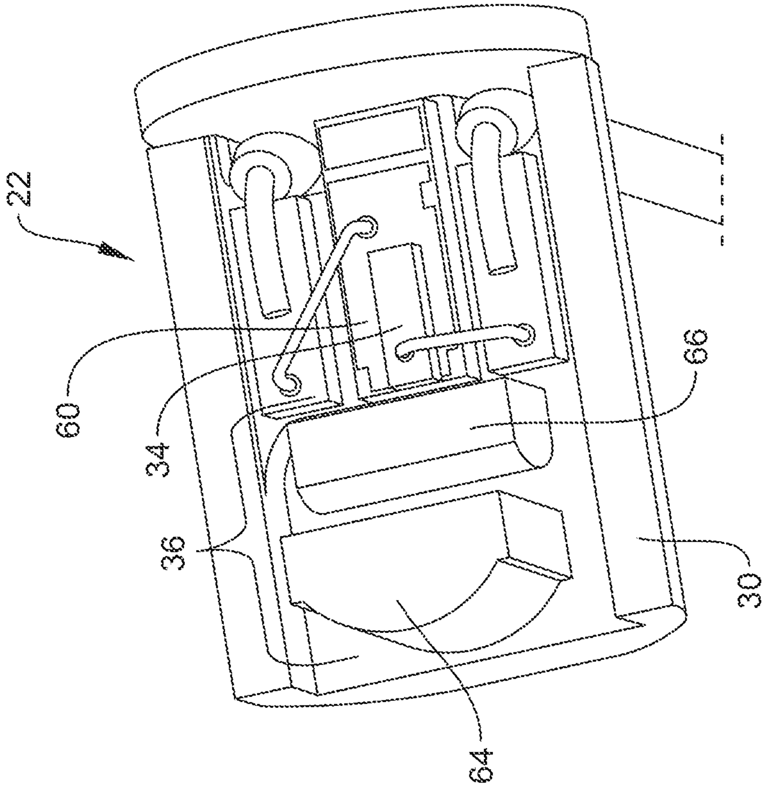

Reference is now made to FIGS. 5A-B, which are schematic illustrations of structured light projector 22 and beam shaping optical element 36, in accordance with some applications of the present invention. Typically, sealed housing 30 is made of metal and semiconductor laser die 34 is disposed within sealed housing 30 such that heat is conducted from semiconductor laser die 34 to the metal of sealed housing 30. For some applications, semiconductor laser die 34 is mounted on a submount 60 within sealed housing 30 such that heat is conducted from semiconductor laser die 34 to the metal of sealed housing 30 through submount 60, i.e., submount 60 acts as a heat sink for semiconductor laser die 34. Submount 60 is typically made of a material with high thermal conductivity, such as ceramic. Submount 60 also may be positioned to act as a pedestal for semiconductor laser die 34, such that emission point 42 of semiconductor laser die is lined up with an optical axis 62 of beam shaping optical element 36 (illustrated in FIG. 2B). For some applications, a length L2 of submount 60 is at least 0.8 mm and/or less than 1.6 mm.

Beam shaping optical element 36 is typically a collimating lens (or a combination of collimating lenses) placed in the emission path of semiconductor laser die 34 in order to change the shape of the naturally elliptical laser beam into a circular beam. FIG. 5A shows beam shaping optical element 36 as a series of two cylindrical lenses, one a fast axis collimating (FAC) lens 64 and one a slow axis collimating (SAC) lens 66. For some applications, FAC lens 66 and SAC lens 64 are two opposing surfaces of a single lens, as shown in FIG. 5B. For some applications, a combination of a cylindrical lens with a spherical lens may be used for beam shaping optical element 36 (configuration not shown).

Figure 6A:
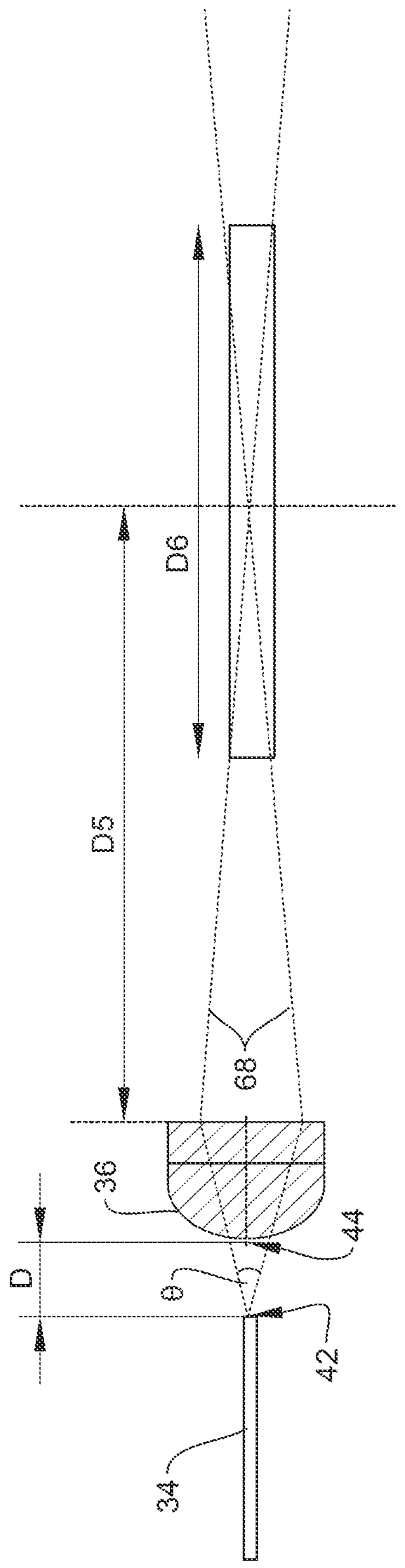
FIG. 6A is a schematic illustration of the relative positioning of a semiconductor laser die of the structured light projector and beam shaping optical element, in accordance with some applications of the present invention.

Reference is now made to FIG. 6A, which is a schematic illustration of the relative positioning of semiconductor laser die 34 and beam shaping optical element 36, in accordance with some applications of the present invention. Typically, the laser beam exiting beam shaping optical element 36 is a Gaussian beam, which converges at some focal distance D5 away from beam shaping optical element 36. For a Gaussian beam (i) of a given divergence angle theta, and (ii) focused by a beam shaping optical element at a given focal distance D5, as a distance between the emission point and the beam shaping optical element decreases, the depth of focus, i.e., the distance over which the Gaussian beam remains focused, increases.

As described hereinabove with reference to FIGS. 2A-C, the placement of beam shaping optical element 36 within sealed housing 30 together with semiconductor laser die 34 enables positioning beam shaping optical element 36 such that a distance D between emission point 42 of semiconductor laser die 34 and input face 44 of beam shaping optical element 36 is very short, e.g., at least 50 microns and/or less than 250 microns.

Figure 6B:
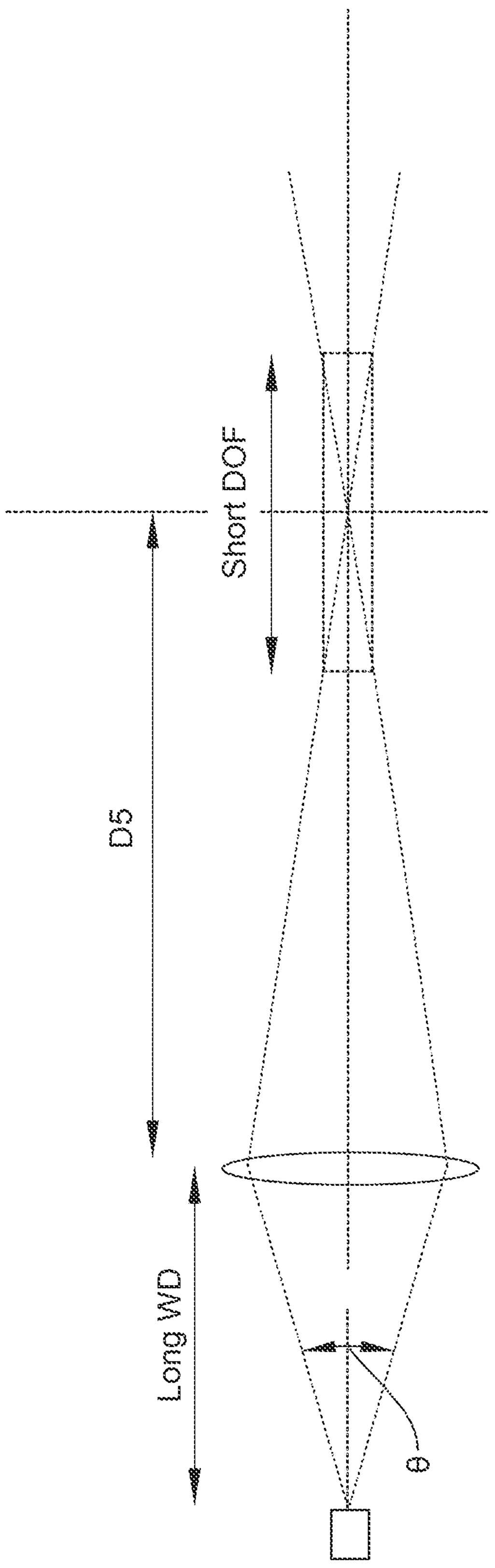
FIG. 6B illustrates depth of focus when utilizing a larger focusing lens aperture.

FIG. 6A shows distance D between emission point 42 and input face 44, and the divergence and subsequent convergence of a Gaussian laser beam 68 emitted from semiconductor laser die 34 and having angle of divergence theta. In general, when focusing a Gaussian beam, for a given focal distance, decreasing the size of a focusing lens aperture increases the depth of focus of the converging laser beam. For a given focal distance D5, the depth of focus D6 is shown is shown in FIG. 6A. FIG. 6B illustrates how the depth of focus would be shorter than D6 for a Gaussian beam (i) of the same divergence angle as Gaussian beam 68, (ii) that is focused at the same focal distance as Gaussian beam 68, but (iii) that utilizes a larger focusing lens aperture due to a larger distance between the emission point of the laser and the focusing lens causing the laser beam to be more diverged when entering the focusing lens. The close placement of beam shaping optical element 36 to emission point 42 of semiconductor laser die 34 enables laser beam 68 to enter beam shaping optical element 36 while laser beam 68 remains narrow, effectively creating a narrow aperture.

It is known in the field of photography that decreasing the size of the aperture increases depth of focus. In some prior art optical systems utilizing lasers, a beam-narrowing aperture may be placed between the laser and the focusing lens in order to reduce the size of the beam. The inventors have realized that the close placement of beam shaping optical element 36 to emission point 42 of semiconductor laser die 34 (described hereinabove) effectively creates a small aperture, resulting in desired depth of focus D6, without the need for physically blocking part of the laser light from entering beam shaping optical element 36. Thus, for some applications, at least 75%, e.g., at least 80% and/or less than 90%, of the light emitted by semiconductor laser die 34 enters beam shaping optical element 36. This high collection efficiency of structured light projector 22 in turn reduces heat buildup within sealed housing 30, thereby lengthening the lifetime of structured light projector 22. Additionally, the higher collection efficiency of structured light projector 22 enables the activating of structured light projector 22 with a lower pulse duty cycle, e.g., a pulse duty cycle of at least 5% and/or less than 25%, yielding an increased number of structured light pattern elements projected onto intraoral surface 28 per second.

Figure 7:
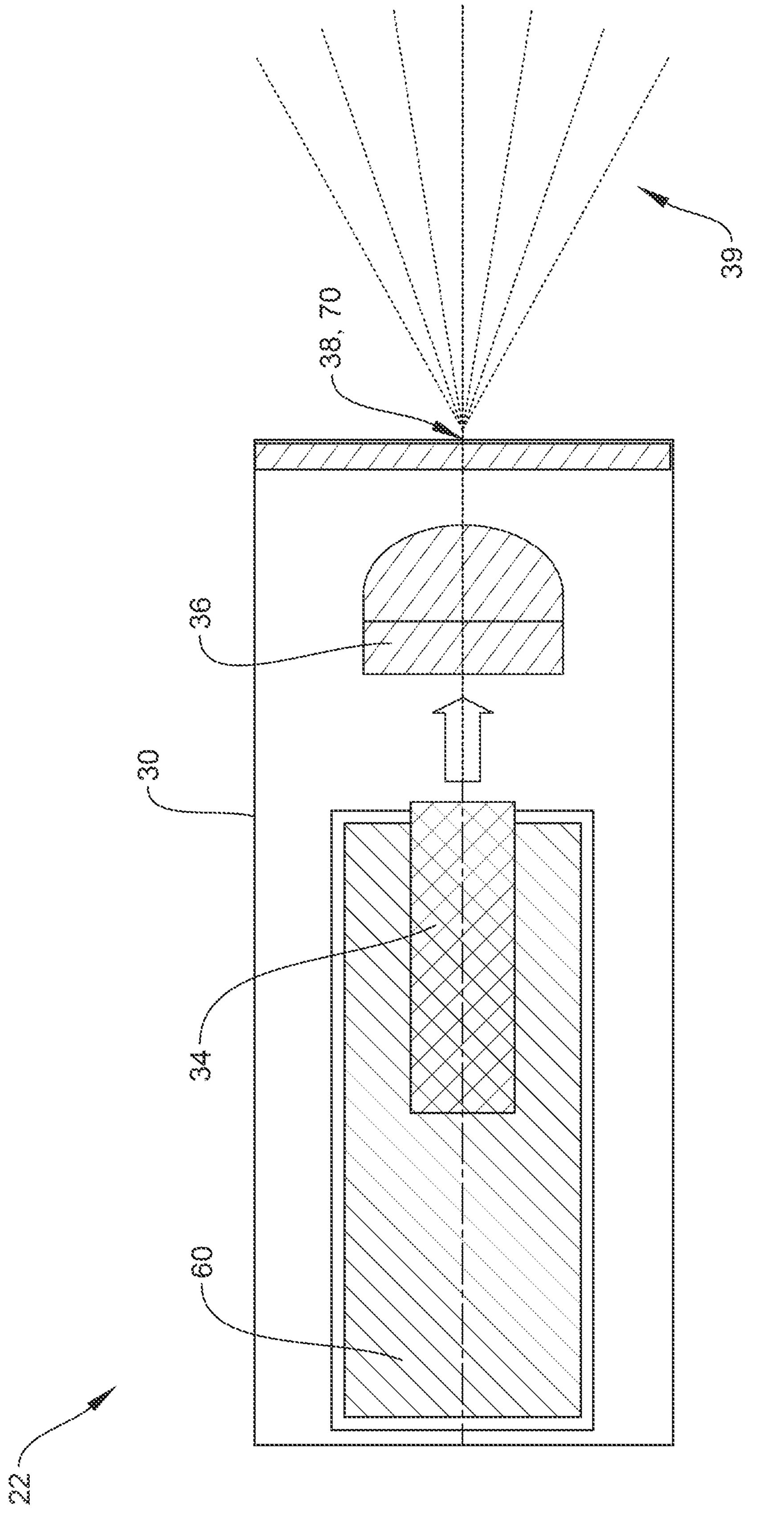
FIG. 7 is a schematic illustration of the structured light projector in accordance with some applications of the present invention.

Reference is now made to FIG. 7, which is a schematic illustration of structured light projector 22 in accordance with some applications of the present invention. Sealed housing 30 comprises a transparent window 70 through which laser light 39 emitted from semiconductor laser die 34 exits sealed housing 30. For some applications, transparent window 70 comprises pattern generating optical element 38, i.e., pattern generating optical element 38 is an area of transparent window 70 of sealed housing 30.

Figure 8:
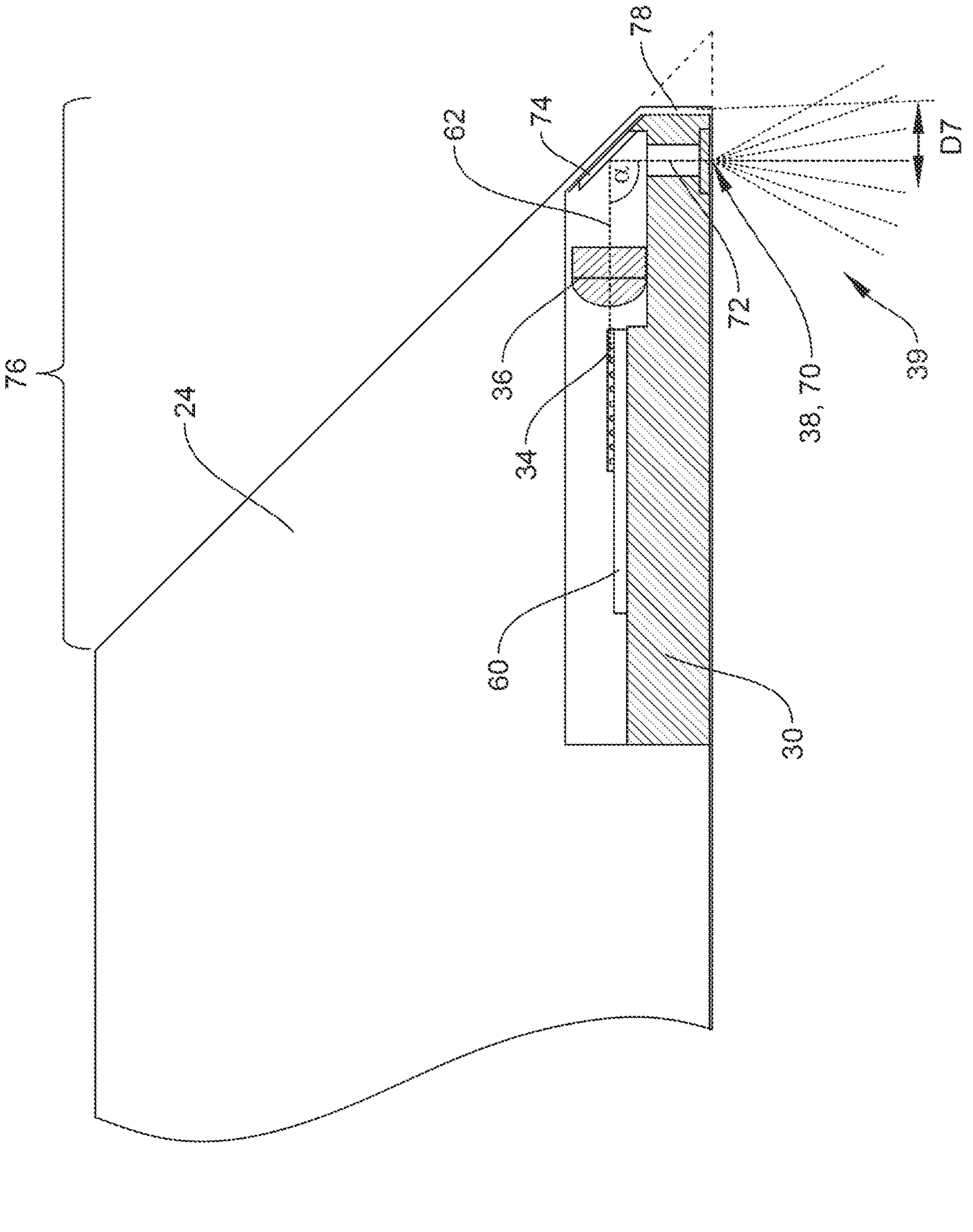
FIG. 8 is a schematic illustration of the structured light projector disposed within the probe, in accordance with some applications of the present invention.

Reference is now made to FIG. 8, which is a schematic illustration of structured light projector 22 disposed with an angled tip 76 of probe 24, in accordance with some applications of the present invention. For some applications, an angle alpha between optical axis 62 of beam shaping optical element 36 and an optical axis 72 of pattern generating optical element 38 is at least 65 degrees and/or less than 120 degrees. FIG. 8 shows a particular example in which angle alpha is 90 degrees and pattern generating optical element 38 is itself transparent window 70 of sealed housing 30. Structured light projector 22 includes a mirror 74 disposed within sealed housing 30 and positioned so as to reflect laser light 39 exiting beam shaping optical element 36 toward pattern generating optical element 38. For some applications, positioning pattern generating optical element 38 such that there is angle alpha between optical axes 62 and 72 enables a more efficient use of space within probe 24. For example, as shown in FIG. 8, use of fold mirror 74 and angle alpha between optical axes 62 and 72 permits sealed housing 30 of structured light projector 22 to be placed into tight spaces such as angled tip 76 of probe 24, resulting in a very small distance D7 between optical axis 72 of pattern generating optical element 38 and a distal-most point 78 of tip 76. For some applications, distance D7 is at least 0.5 mm and/or less than 3 mm.

Figure 9:
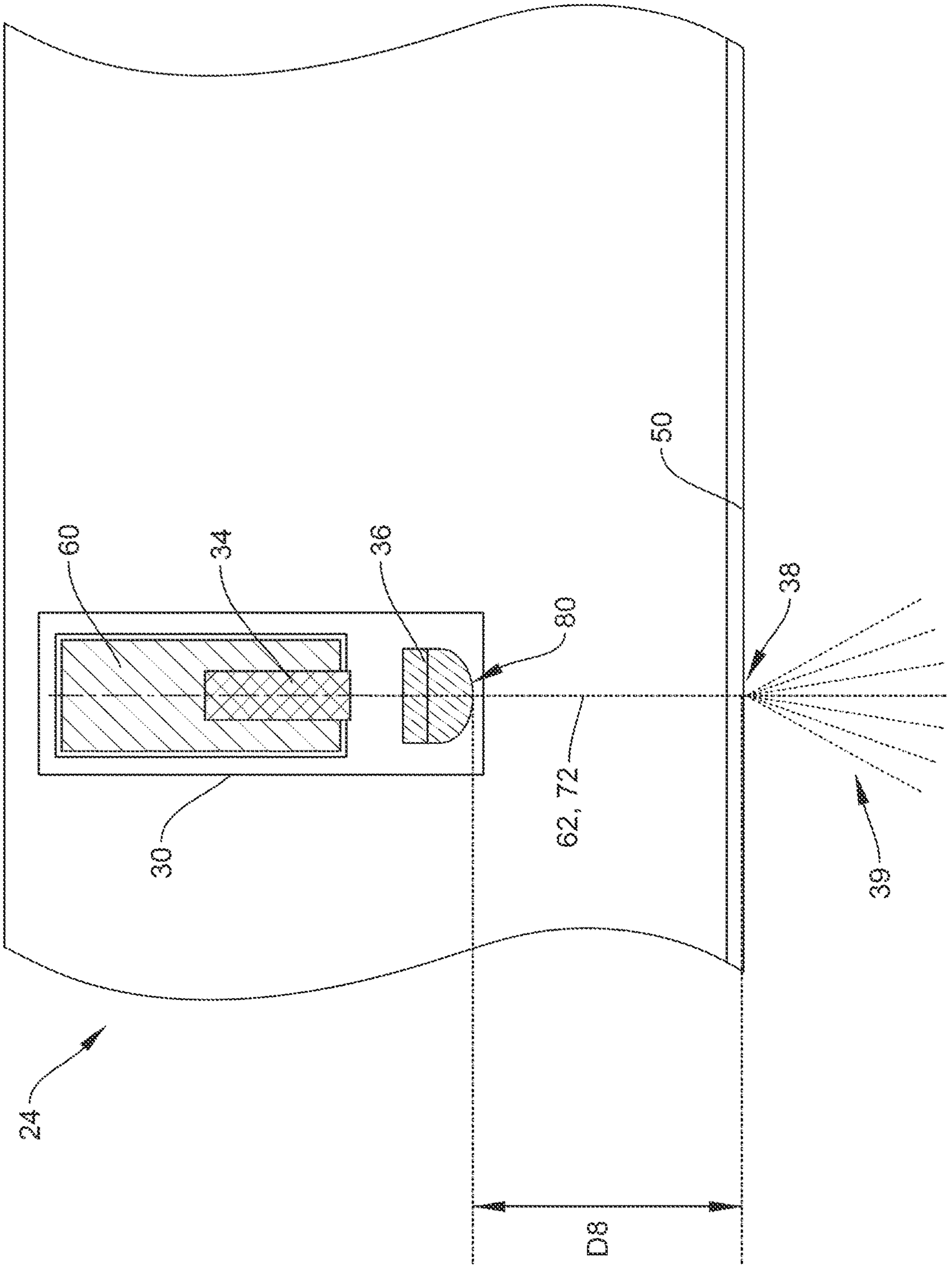
FIG. 9 is a schematic illustration of the structured light projector disposed within the probe, in accordance with some applications of the present invention.

Reference is now made to FIG. 9, which is a schematic illustration of structured light projector 22 disposed within probe 24, in accordance with some applications of the present invention. As described hereinabove with reference to FIGS. 2A-C, the placement of beam shaping optical element 36 within sealed housing 30 together with semiconductor laser die 34 enables positioning beam shaping optical element 36 such that a distance D between emission point 42 of semiconductor laser die 34 and input face 44 of beam shaping optical element 36 is very short, e.g., at least 50 microns and/or less than 250 microns, in turn enabling a reduction in overall size of structured light projector 22. The smaller size of structured light projector 22 in turn permits the space within probe 24 to position pattern generating optical element 38 farther away from beam shaping optical element 36. For some applications, pattern generating optical element 38 is disposed within probe 24 outside of sealed housing 30, such that a distance D8 laser light 39 travels from exiting beam shaping optical element 36 to entering pattern generating optical element 38 is at least 2 mm, e.g., at least 8 mm, and/or less than 25 mm away from transparent window 70 of sealed housing 30. FIG. 9 shows an example where pattern generating optical element is disposed at transparent window 50 of probe 24, and sealed housing 30 disposed within probe 24 such that an output face 80 of beam shaping optical element 36 is at distance D8 from transparent window 50 of probe 24.

Typically, the laser beam exiting beam shaping optical element 36 is a Gaussian beam, which converges at some focal distance away from beam shaping optical element 36. For a Gaussian beam (i) of a given divergence angle, and (ii) focused by a beam shaping optical element of a given aperture size, as the focal distance of the Gaussian beam increases, the depth of focus, i.e., the distance over which the Gaussian beam remains focused, increases. The inventors have realized that increasing the distance between beam shaping optical element 36 and pattern generating optical element 38 increases the focal distance of laser light 39, in turn increasing the depth of focus.

Figure 10:
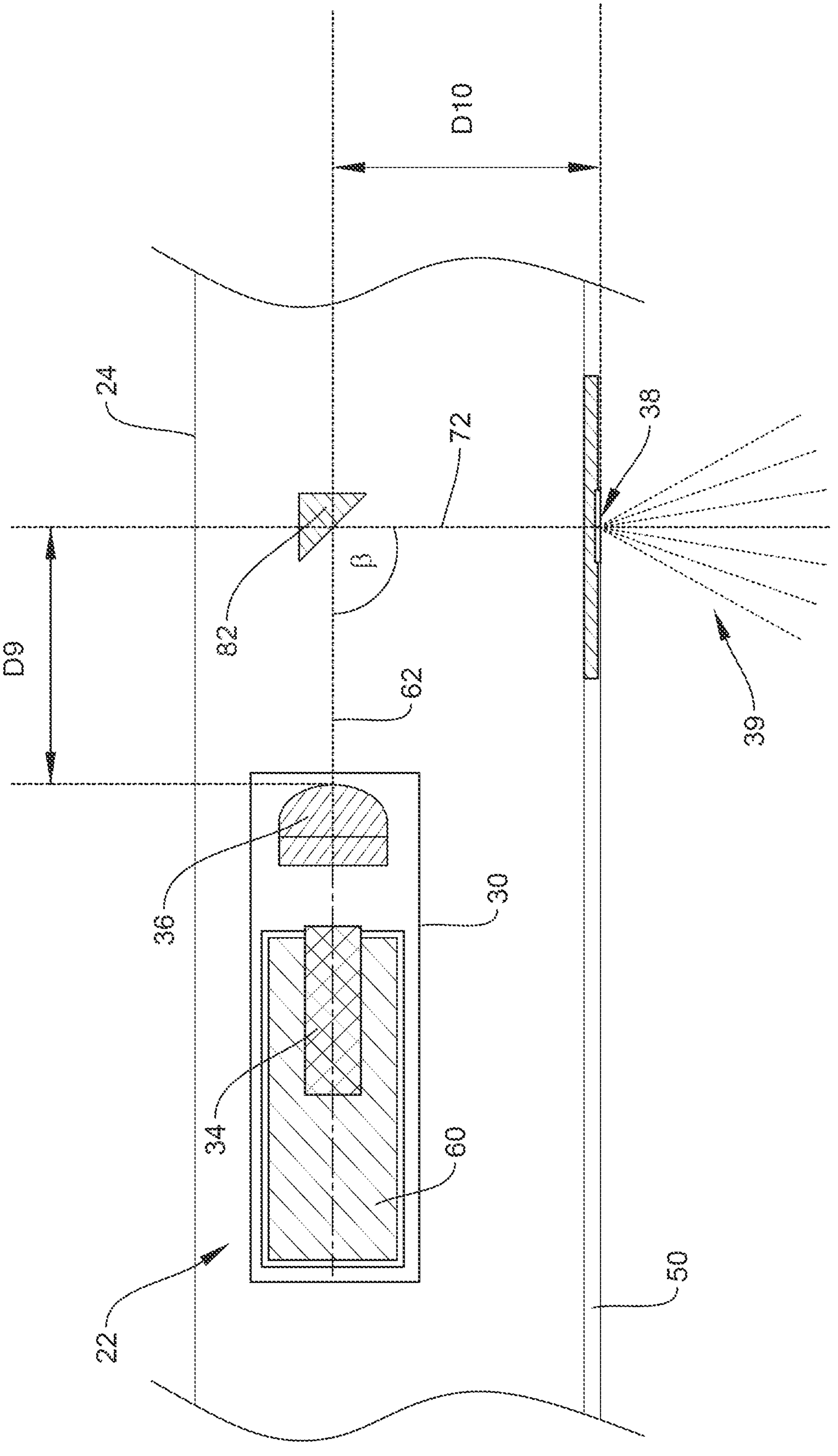
FIG. 10 is a schematic illustration of the structured light projector disposed within the probe, in accordance with some applications of the present invention.

Reference is now made to FIG. 10, which is a schematic illustration of structured light projector 22 disposed within probe 24, in accordance with some applications of the present invention. For some applications, pattern generating optical element 38 is disposed within probe 24 outside of sealed housing 30 such that an angle beta between optical axis 62 of beam shaping optical element 36 and optical axis 72 of pattern generating optical element 38 is at least 50 degrees and/or less than 100 degrees. A fold mirror 82 is disposed within probe 24 and positioned so as to reflect laser light 39 exiting beam shaping optical element 36 toward pattern generating optical element 38. A total distance D9+D10 that laser light 39 travels from exiting beam shaping optical element 36 to entering pattern generating optical element 38 is at least 8 mm and/or less than 25 mm.

Reference is now made to FIGS. 11-16, which are schematic illustrations of structured light projector 22 with light source 32 including a first semiconductor laser die 84 and a second semiconductor laser die 86 both disposed within sealed housing 30 of structured light projector 22, in accordance with some applications of the present invention. The inventors have realized that by mounting more than one semiconductor laser die within sealed housing 30 the number of structured light projectors within probe 24 is effectively increased without taking up further space within probe 24. Additional benefits of multiple laser dies mounted within sealed housing 30 are described hereinbelow with respect to specific examples. For some applications for at least one of structured light projectors 22, light source 32 includes first semiconductor laser die 84 and second semiconductor laser die 86. For some applications, first semiconductor laser die 84 and second semiconductor laser die 86 are mounted to a common submount 60 within sealed housing 30, as illustrated in FIGS. 11-16.

Figure 11:
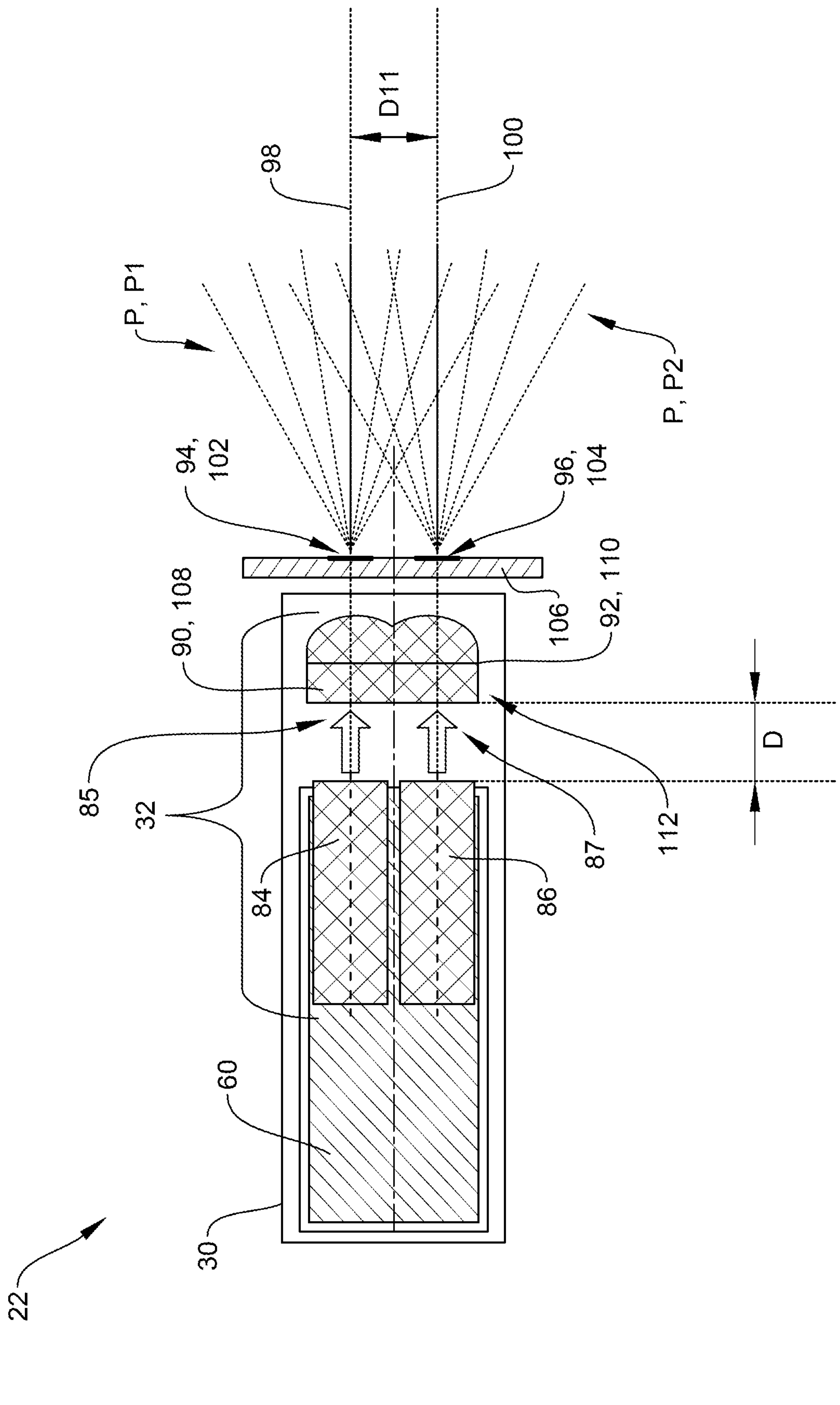
FIGS. 11-16 are schematic illustrations of the structured light projector with a light source including a first semiconductor laser die and a second semiconductor laser die, in accordance with some applications of the present invention.
Figure 12:
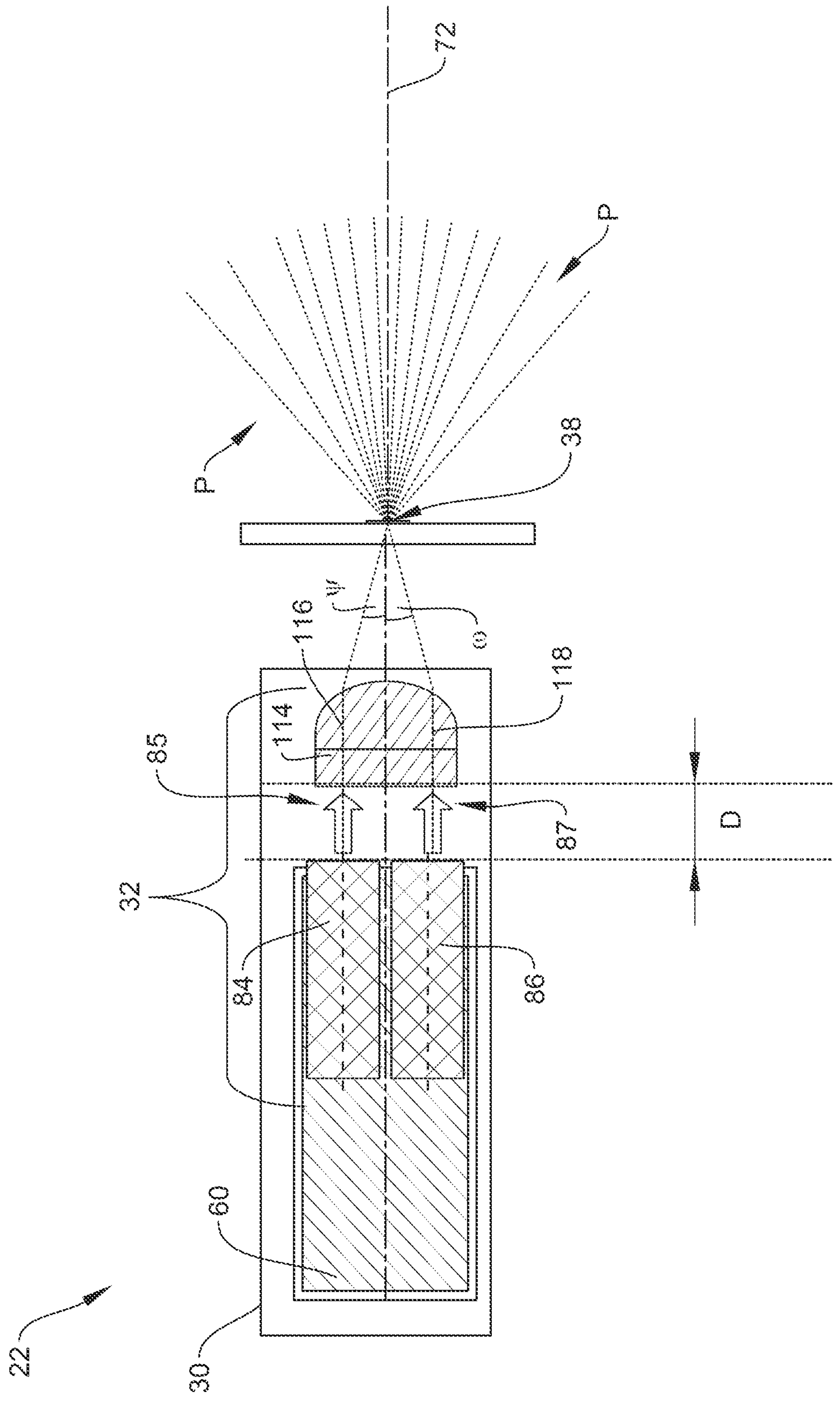

Reference is now specifically made to FIGS. 11-12. For some applications, first and second semiconductor laser dies 84 and 86 have different wavelengths, i.e., they project laser light of different colors. For example, first semiconductor laser die 84 may be a blue laser and second semiconductor laser die 86 may be a green laser. A computer processor 88 (shown in FIG. 1) activates first and second semiconductor laser dies 84 and 86 such that structured light projector 22 projects a pattern P in each of the two different wavelengths.

Reference is now made specifically to FIG. 11. For some applications, first and second semiconductor laser dies 84 and 86 each have their own respective beam shaping optical element and pattern generating optical element. That is, laser light 85 from first semiconductor laser die 84 enters and subsequently exits a first beam shaping optical element 90 and laser light 87 from second semiconductor laser die 86 enters and subsequently exits a second beam shaping optical element 92. First and second beam shaping optical elements 90 and 92 typically each have the same characteristics as beam shaping optical element 36 described hereinabove. First and second pattern generating optical elements 94 and 96 are arranged such that laser light 85 exiting first beam shaping optical element 90 enters first pattern generating optical element 94 and laser light 87 exiting second beam shaping optical element 92 enters second pattern generating optical element 96. It is noted that distance D between emission point 42 of semiconductor laser die 34 and input face 44 of beam shaping optical element 36 described hereinabove applies to first and second beam shaping optical elements 90 and 92, mutatis mutandis.

For some applications, first and second pattern generating optical elements 94 and 96 project the same pattern P of light, such that structured light projector 22 projects (a) pattern P of light in the first wavelength in a first position onto intraoral surface 28 and (b) pattern P of light in the second wavelength translationally shifted with respect to the first position onto intraoral surface 28. Typically, the projected pattern P of light in the second wavelength is translationally shifted with respect to the first position by a distance D11 between respective optical axes 98 and 100 of first and second pattern generating optical elements 94 and 96. For some applications, first and second pattern generating optical elements 94 and 96 project different patterns of light, such that structured light projector 22 projects (a) a first pattern P1 from first pattern generating optical element 94 in a first position onto intraoral surface 28, and (b) a second pattern P2 (different from first pattern P1) from second pattern generating optical element 96 translationally shifted with respect to the first position onto intraoral surface 28.

For some applications, first and second semiconductor laser dies 84 and 86 are mounted within sealed housing 30 such that first and second semiconductor laser dies 84 and 86 respectively emit laser light 85 and 87 in the same direction. For some applications, first and second pattern generating optical elements 94 and 96 are respective first and second areas 102 and 104 of a common lens 106. It is noted that all the options described hereinabove regarding the positioning of pattern generating optical element 38 apply to first and second pattern generating optical elements 94 and 96, mutatis mutandis.

For some applications, first and second beam shaping optical elements 90 and 92 are respective first and second areas 108 and 110 of a common lens 112. Alternatively, first and second beam shaping optical elements 90 and 92 are separate lenses (configuration not shown).

For some applications, computer processor 88 concurrently activates first and second semiconductor laser dies 84 and 86, such that the structured light projector 22 concurrently projects pattern P, or first and second patterns P1 and P2, in each of the two different wavelengths. The translational shift (described hereinabove) between the projected patterns of light as well as the difference in wavelength between the patterns of light, result in a dense distribution of structured light elements for digital 3D reconstruction of intraoral surface 28, while reducing interference between the patterns.

Alternatively, for some applications, computer processor 88 alternatingly activates first and second semiconductor laser dies 84 and 86 such that structured light projector 22 alternatingly projects pattern P, or first and second patterns P1 and P2, in each of the two different wavelengths. Activating first and second semiconductor laser dies 84 and 86 in an alternating time-share provides the advantage of a dense distribution of structured light elements for use in digital 3D reconstruction of intraoral surface 28 while reducing the amount of light projected into the intraoral cavity at any given time. This in turn helps to maintain contrast that may otherwise be reduced by the reflective and somewhat translucent nature of teeth.

Reference is now specifically made to FIG. 12. For some applications, first and second semiconductor laser dies 84 and 86 share a common beam shaping optical element 114. Beam shaping optical element 114 is arranged such that laser light 85 and 87 from each of first and second semiconductor laser dies 84 and 86, respectively, (i) enters beam shaping optical element 114 along different respective axes 116 and 118 of beam shaping optical element 114, and (ii) subsequently impinges on pattern generating optical element 38 at different respective angles psi and omega, such that projected pattern P in each wavelength is angularly shifted about an optical axis 72 of pattern generating optical element 38. It is noted that distance D between emission point 42 of semiconductor laser die 34 and input face 44 of beam shaping element 36 described hereinabove applies to beam shaping optical element 114, mutatis mutandis.

For some applications, computer processor 88 concurrently activates first and second semiconductor laser dies 84 and 86, such that structured light projector 22 concurrently projects pattern P in each of the two different wavelengths. The angular shift between the projected patterns of light as well as the difference in wavelength between the patterns of light, result in a dense distribution of structured light elements for digital 3D reconstruction of intraoral surface 28, while reducing interference between the patterns.

Alternatively, for some applications, computer processor 88 alternatingly activates first and second semiconductor laser dies 84 and 86 such that structured light projector 22 alternatingly projects pattern P in each of the two different wavelengths. Activating first and second semiconductor laser dies 84 and 86 in an alternating time-share provides the advantage of a dense distribution of structured light elements for use in digital 3D reconstruction of intraoral surface 28 while reducing the amount of light projected into the intraoral cavity at any given time. This in turn helps to maintain contrast that may otherwise be reduced by the reflective and somewhat translucent nature of teeth. Activating first and second semiconductor laser dies 84 and 86 in an alternating time-share also provides the advantage of a dense distribution of structured light elements for digital 3D reconstruction of intraoral surface 28, while reducing interference between the patterns.

Figure 13:
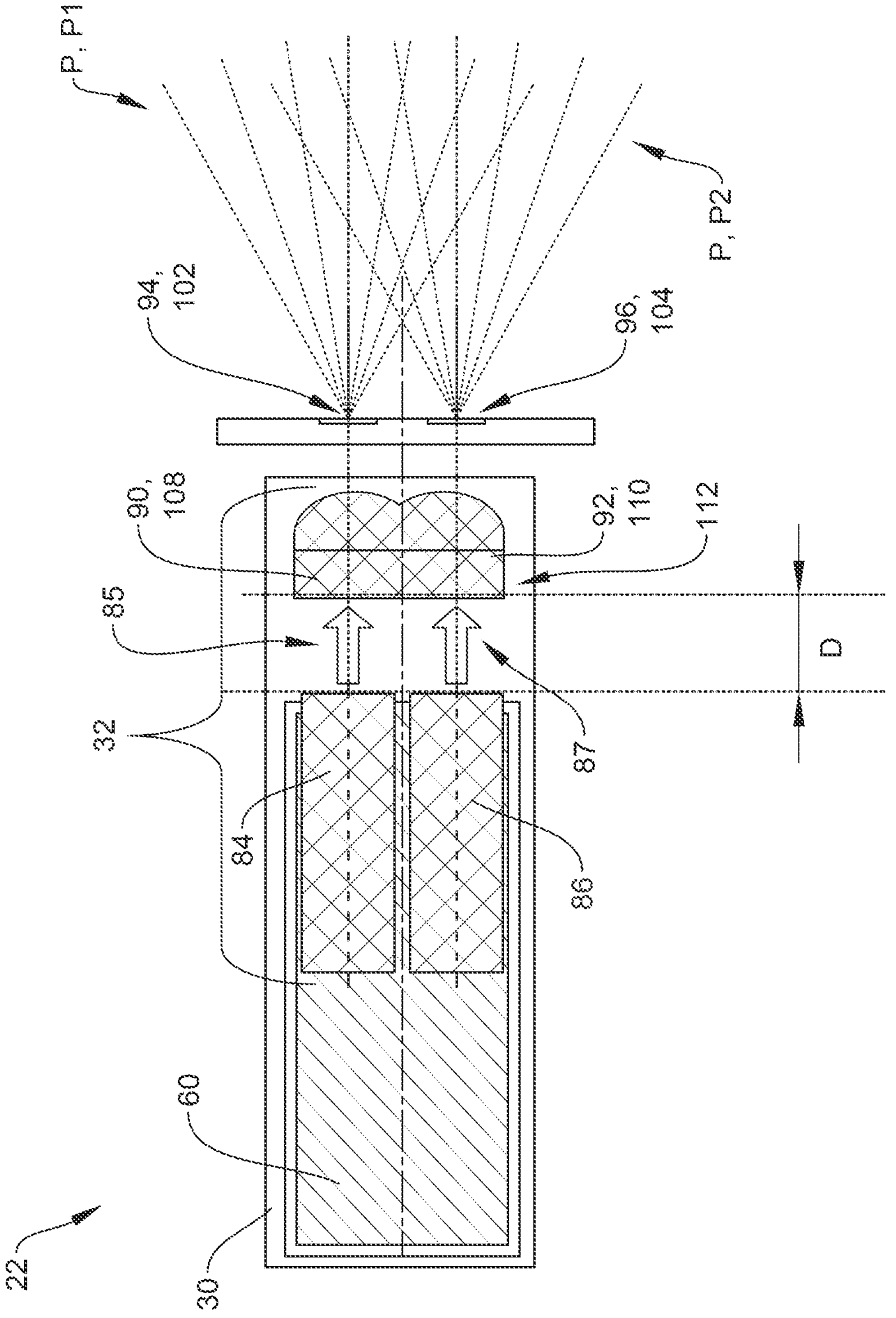
Figure 14A:
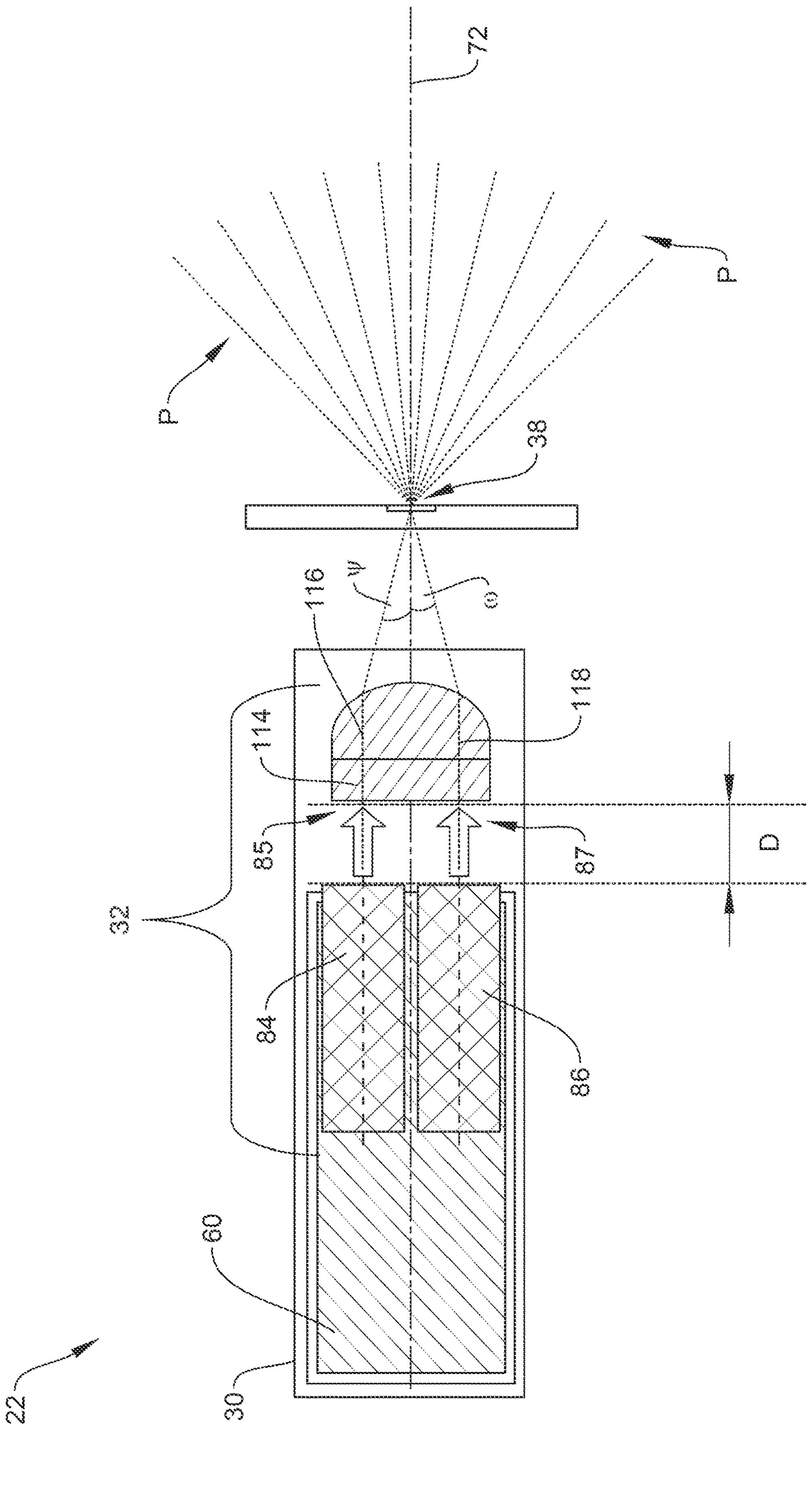
Figure 14B:
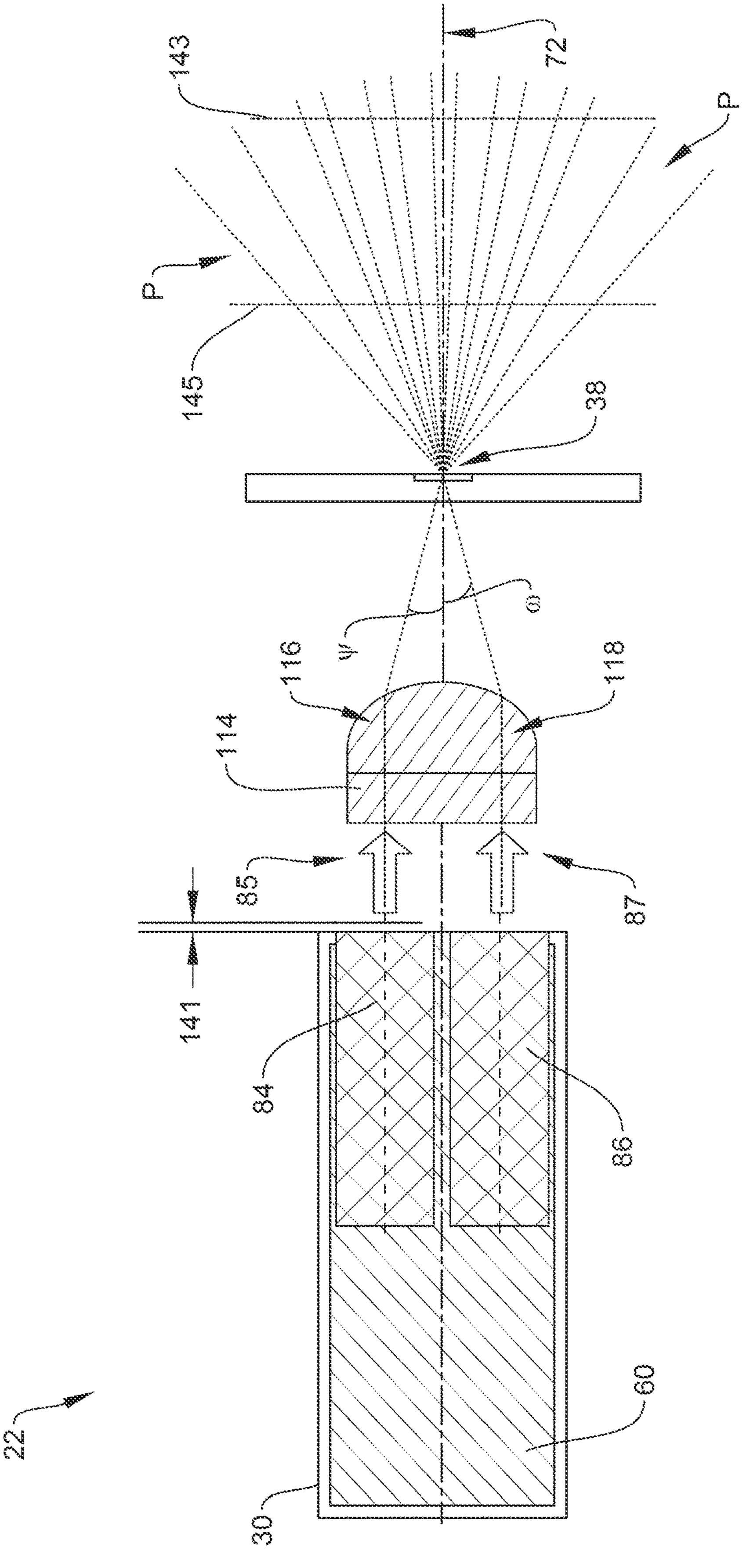

Reference is now specifically made to FIGS. 13-14B. For some applications, first and second semiconductor laser dies 84 and 86 have the same wavelength, i.e., they project laser light of the same color. Computer processor 88 (shown in FIG. 1) typically alternatingly activates first and second semiconductor laser dies 84 and 86 having the same wavelength. FIG. 13 shows first and second semiconductor laser dies 84 and 86 having respective beam shaping optical elements 90 and 92 and respective pattern generating optical elements 94 and 96, such as described hereinabove with reference to FIG. 11, mutatis mutandis.

FIGS. 14A-B show first and second semiconductor laser dies 84 and 86 sharing common beam shaping optical element 114, such as described hereinabove with reference to FIG. 12, mutatis mutandis.

For some applications, semiconductor laser dies 84 and 86 have the same wavelength, share common beam shaping optical element 114, and angles psi and omega are equal to an integer multiple of the diffraction angle of pattern generating optical element 38, such that the two patterns P overlap. In this case, computer processor 88 may concurrently activate semiconductor laser dies 84 and 86 having the same wavelength. The overlapping patterns P of the same wavelength may result in generally the same number of structured light features projected onto intraoral surface 28 as when only one of semiconductor laser dies is activated, but with reduced speckle noise.

With reference to FIG. 14B, in one embodiment a dual focus projector is implemented. For the dual focus projector, there is an axial offset 141 between first semiconductor laser die 84 and second semiconductor laser die 86. The axial offset results in a two focal planes or focal surfaces. The first semiconductor laser die 84 (which has a greater distance from the shared common beam shaping optical element 114) has a first focal surface 143. The second semiconductor laser die 86 (which has a lesser distance from the shared common beam shaping optical element 114) has a second focal surface 145. In some embodiments, the focal surfaces are focal planes. In some embodiments, the focal surfaces are non-flat focal surfaces (e.g., spherical focal surfaces). As shown, the first focal surface 143 has a greater distance from the pattern generating optical element 38 than the second focal surface 145 due to the axial offset 141. Accordingly, the axial offset results in the first semiconductor laser die 84 being associated with first focal surface 143 and the second semiconductor laser die 86 being associated with a different second focal surface 145. In one embodiment, the axial offset 141 is between about 1 μm and about 6 μm (e.g., 1 μm, 2 μm, 3 μm, 4 μm, 5 μm, 6 μm, and so on). In one embodiment, an offset between the first focal surface 143 and second focal surface 145 is about 1.7 mm to about 10 mm (e.g., 1.7 mm, 2 mm, 3 mm, 4 mm, 5 mm, 6 mm, 7 mm, 8 mm, 9 mm, 10 mm, and so on).

In some embodiments, the first semiconductor laser die 84 and second semiconductor laser die 86 are operated in parallel (e.g., simultaneously). In some embodiments, first semiconductor laser die 84 and second semiconductor laser die 86 are operated in series. In an example, structured light projector 22 may alternate between activation of first semiconductor laser die 84 and second semiconductor laser die 86 over time (e.g., perform time alternation between the first semiconductor laser die 84 and second semiconductor laser die 86). Such time alternation between the first semiconductor laser die 84 and second semiconductor laser die 86 results in bi-focus projection in embodiments. Such bi-focus projection may be similar to the bi-focus projection that can be achieved using a focusing mechanism that changes the focus over time (e.g., by changing a position of a focusing lens), but without any moving parts.

In one embodiment, computer processor 88 alternatingly activates first and second semiconductor laser dies 84 and 86 such that structured light projector 22 alternatingly projects pattern P, or first and second patterns P1 and P2, at different focal planes 143, 145. In one embodiment, computer processor 88 alternatingly activates first and second semiconductor laser dies 84 according to a pre-programmed sequence. In one embodiment, computer processor 88 alternatingly activates first and second semiconductor laser dies 84 dynamically based on one or more distances to a measured object and/or based on other properties of the measured object.

Figure 15:
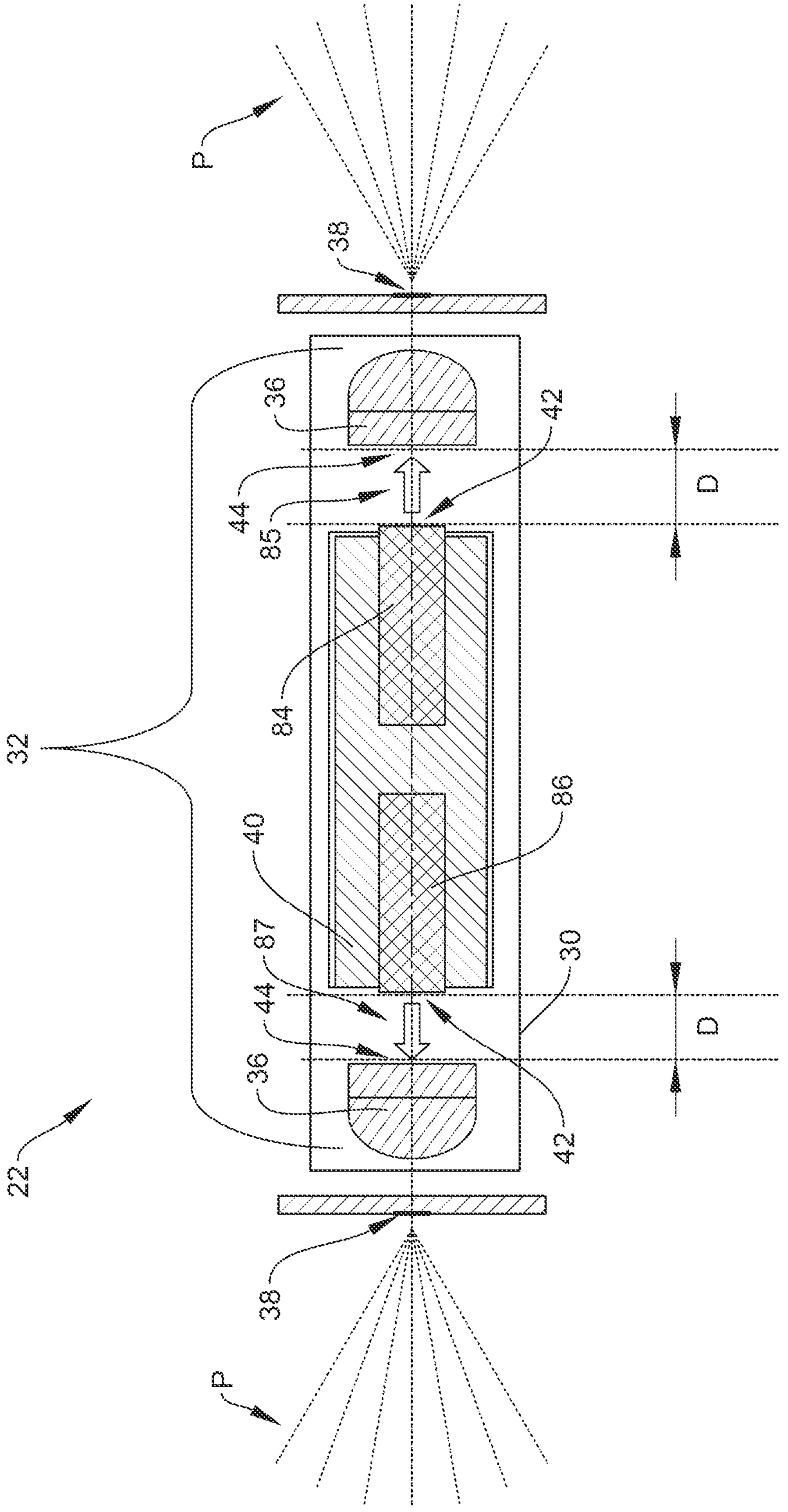

Reference is now specifically made to FIG. 15. For some applications, first semiconductor laser die 84 and second semiconductor laser die 86 are mounted within sealed housing 30, e.g., on common submount 60 within sealed housing 30, such that first and second semiconductor laser dies 84 and 86 emit laser light 85 and 87 in different directions, effectively creating two separate structured light projectors without having to take up extra space within probe 24. For some applications, first and second semiconductor laser dies 84 and 86 are arranged such that they emit laser light 85 and laser light 87 in opposite directions. When computer processor 88 activates first and second semiconductor laser dies 84 and 86, structured light projector 22 projects a first pattern P in the first direction and a second pattern P in the second direction.

Light source 32 includes two separate beam shaping optical elements 36, arranged such that laser light 85 from first semiconductor laser die 84 and laser light 87 from second semiconductor laser die 86 enters and subsequently exits a respective beam shaping optical element 36. It is noted that distance D, as described hereinabove, between the emission point 42 of the semiconductor laser die and input face 44 of the beam shaping optical element, applies to both beam shaping optical elements 36 as depicted in FIG. 15, mutatis mutandis. Structured light projector 22 includes a first and second pattern generating optical element 38 arranged such that laser light 85 and laser light 87 respectively enter first and second pattern generating optical elements 38. For some applications, first and second semiconductor laser dies 84 and 86 have the same wavelength. Alternatively, for some applications, first and second semiconductor laser dies 84 and 86 have different wavelengths.

For some applications, computer processor 88 activates first and second semiconductor laser dies 84 and 86 such that structured light projector 22 alternatingly projects the first pattern P in the first direction and the second pattern P in the second direction. Alternatively, for some applications, computer processor 88 activates first and second semiconductor laser dies such that structured light projector 22 projects, at the same time, first pattern P in the first direction and second pattern P in the second direction.

Figure 16:
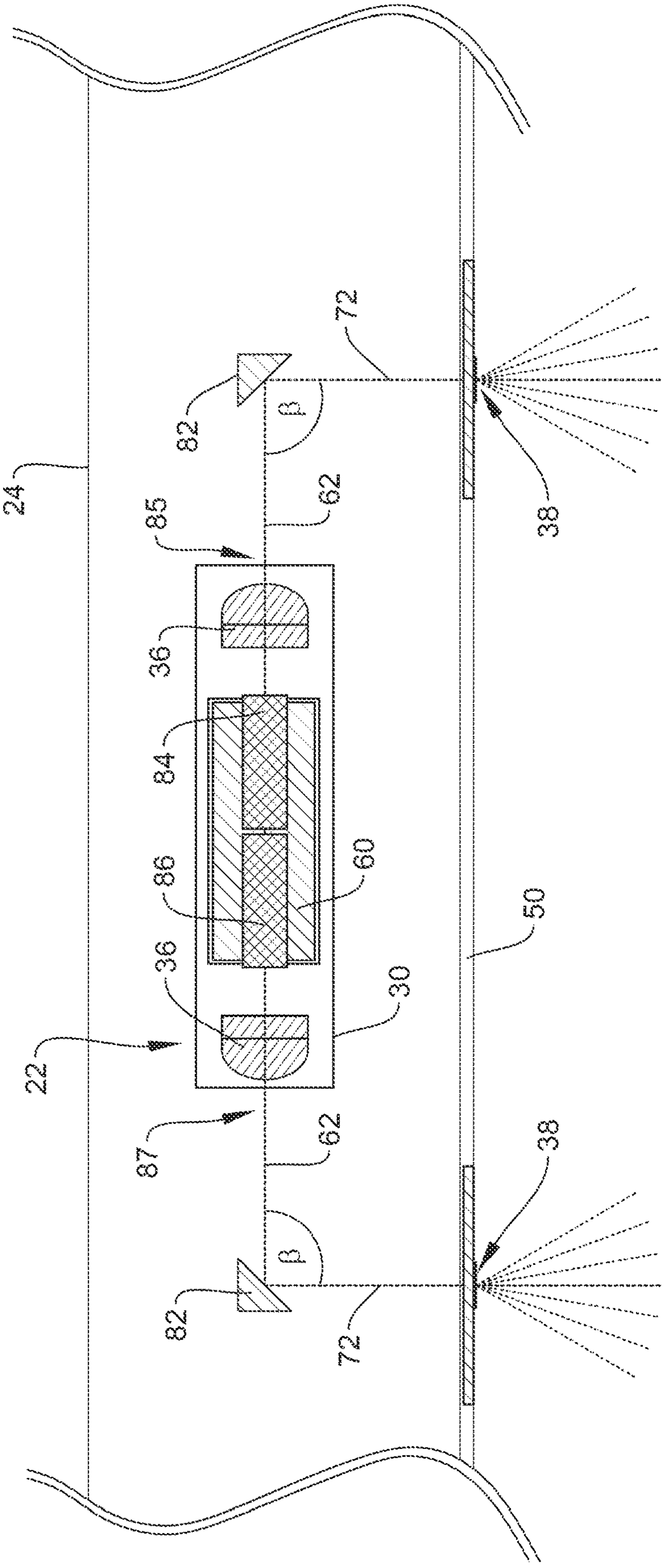

Reference is now made specifically to FIG. 16. FIG. 16 shows a particular example in which first and semiconductor laser dies 84 and 86 are mounted to common submount 60 within sealed housing 30, and respective first and second pattern generating optical elements 38 are each disposed such that there is a respective angle beta, between (a) respective optical axes 62 of each beam shaping optical element 36 and (b) respective optical axes 72 of each pattern generating optical element 38, that is at least 50 degrees and/or less than 100 degrees. Respective fold mirrors 82 are disposed within probe 24 and positioned so as to reflect laser light 85 and 87 exiting respective beam shaping optical elements 36 toward respective pattern generating optical elements 38. It is noted that everything described hereinabove with reference to FIG. 10, relating to the total distance that the laser light travels from exiting the beam shaping optical element to entering the pattern generating optical element, applies to the example of FIG. 16, mutatis mutandis. It is noted that distance D between emission point 42 of semiconductor laser die 34 and input face 44 of beam shaping element 36 described hereinabove applies to first and second beam shaping optical elements 36 depicted in FIG. 16, mutatis mutandis.

Figure 17:
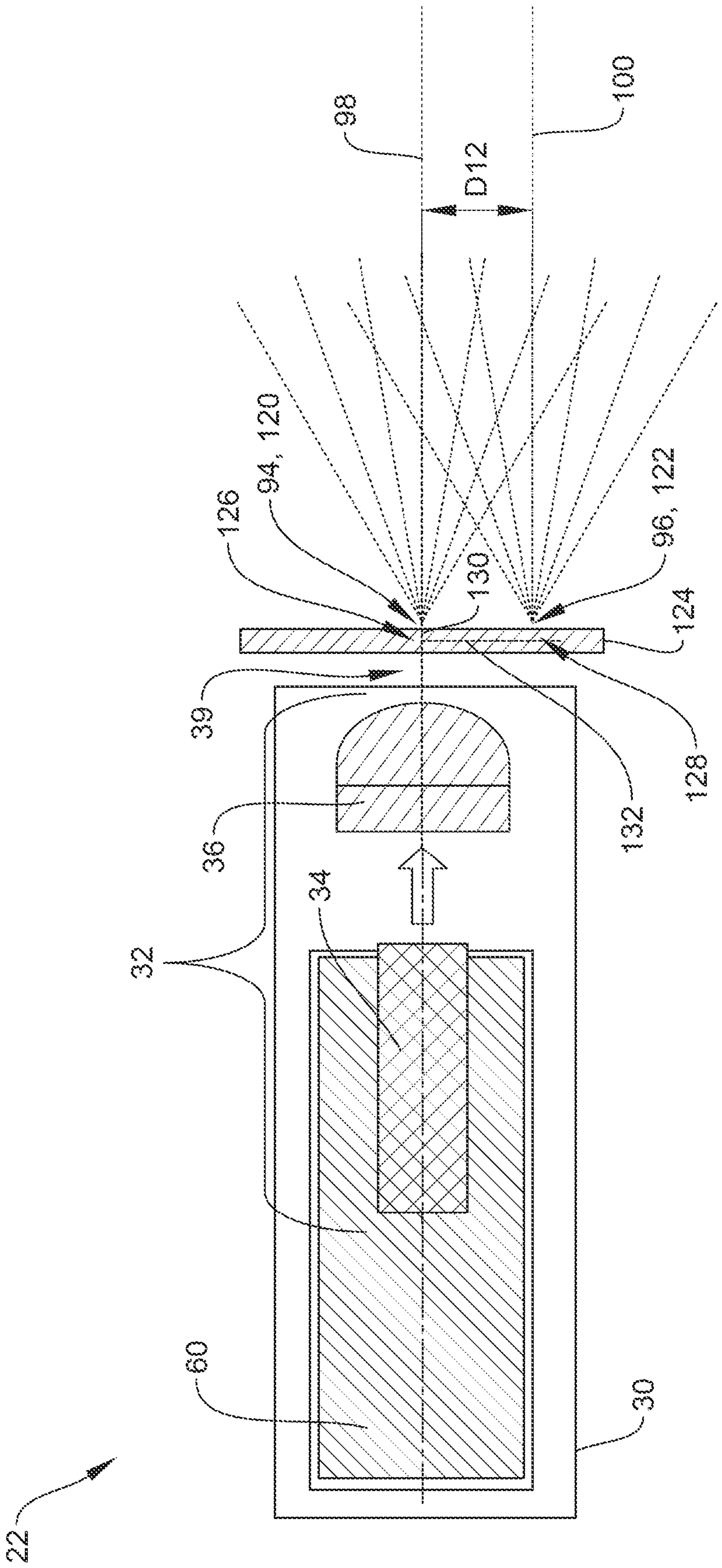
FIG. 17 is a schematic illustration of the structured light projector with a single semiconductor laser die and a split pattern generating optical element, in accordance with some applications of the present invention.

Reference is now made to FIG. 17, which is a schematic illustration of structured light projector 22 with a single semiconductor laser die 34, a single beam shaping optical element 36, and respective first and second pattern generating optical elements 94 and 96, in accordance with some applications of the present invention. For some applications, first and second pattern generating optical elements 94 and 96 are two respective areas 120 and 122 on a common substrate 124 that comprises a beam splitter 126 and a reflector 128 disposed within substrate 124. When computer processor 88 activates semiconductor laser die 34, laser light 39 exiting light source 32 is split by beam splitter 126 into a first beam 130 and a second beam 132 within substrate 124. First beam 130 enters first pattern generating optical element 94 and second beam 132 is reflected by reflector 128 toward second pattern generating optical element 96 to yield two separate projected patterns P that are translationally shifted with respect to each other by a distance D12 between optical axes 98 and 100 of first and second pattern generating optical elements 94 and 96. Together the two separate projected patterns result in structured light projector 22 having a wider field of view.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 88. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., computer processor 88) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 88) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

Computer processor 88 is typically a hardware device programmed with computer program instructions to produce a special purpose computer. For example, when programmed to perform the methods described herein, the computer processor typically acts as a special purpose computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An apparatus for intraoral scanning, the apparatus comprising:

an elongate wand comprising a probe at a distal end of the elongate wand; and one or more structured light projectors disposed within the probe, each structured light projector comprising:

(a) a housing comprising a transparent window through which light exits the housing;

(b) a light source disposed within the housing and comprising:

a semiconductor laser die; and a beam shaping optical element; and (c) a pattern generating optical element, wherein:

the transparent window comprises the pattern generating optical element, a distance D between an emission point of the semiconductor laser die and an input face of the beam shaping optical element is 50-250 microns, and each structured light projector is configured to project a pattern of light onto an intraoral surface when the light source of the structured light projector is activated to emit light through the pattern generating optical element of the structured light projector.

2. The apparatus according to claim 1, wherein for at least one structured light projector of the one or more structured light projectors the semiconductor laser die and the beam shaping optical element being disposed within the housing and the distance D being 50-250 microns together result in a longest dimension of the housing being 1.5-2.5 mm.

3. The apparatus according to claim 1, wherein for at least one structured light projector of the one or more structured light projectors the beam shaping optical element is positioned within the housing such that at least 75% of the light emitted by the semiconductor laser die enters the beam shaping optical element.

4. The apparatus according to claim 3, wherein for at least one structured light projector of the one or more structured light projectors the beam shaping optical element is positioned within the housing such that 80-90% of the light emitted by the semiconductor laser die enters the beam shaping optical element.

5. The apparatus according to claim 1, wherein for at least one structured light projector of the one or more structured light projectors the housing comprises metal and the semiconductor laser die is disposed within the housing such that heat is conducted from the semiconductor laser die to the metal of the housing.

6. The apparatus according to claim 1, further comprising one or more cameras disposed within the probe, wherein a distance between (i) an optical axis of at least one camera and (ii) an optical axis of at least one structured light projector that is adjacent to the at least one camera is 3-5 mm.

7. The apparatus according to claim 6, wherein the one or more structured light projectors project light through the transparent window, through which the one or more cameras receive light, and a distance from the transparent window at which 50% of respective fields of view of the at least one camera and the at least one adjacent structured light projector overlap is 2-6 mm.

8. The apparatus according to claim 6, wherein the one or more structured light projectors project light through the transparent window, through which the one or more cameras receive light, and a distance from the transparent window at which respective fields of view of the at least one camera and the at least one adjacent structured light projector start to overlap is 1-3 mm.

9. The apparatus according to claim 1, wherein for at least one structured light projector of the one or more structured light projectors:

an angle between an optical axis of the beam shaping optical element and an optical axis of the pattern generating optical element is 65-120 degrees, and the apparatus further comprises a mirror disposed within the housing and positioned so as to reflect the light exiting the beam shaping optical element toward the pattern generating optical element.

10. An apparatus for intraoral scanning, the apparatus comprising:

an elongate wand comprising a probe at a distal end of the elongate wand; and one or more structured light projectors disposed within the probe, each structured light projector comprising:

(a) a housing;

(b) a light source disposed within the housing and comprising:

a semiconductor laser die; and a beam shaping optical element; and (c) a pattern generating optical element, wherein:

the pattern generating optical element is disposed within the probe outside of the housing, a distance D between an emission point of the semiconductor laser die and an input face of the beam shaping optical element is 50-250 microns, a distance the light travels from exiting the beam shaping optical element to entering the pattern generating optical element is 2-8 mm, and each structured light projector is configured to project a pattern of light onto an intraoral surface when the light source of the structured light projector is activated to emit light through the pattern generating optical element of the structured light projector.

11. An apparatus for intraoral scanning, the apparatus comprising:

an elongate wand comprising a probe at a distal end of the elongate wand; and one or more structured light projectors disposed within the probe, each structured light projector comprising:

(a) a housing;

(b) a light source disposed within the housing and comprising:

a semiconductor laser die; and a beam shaping optical element; and (c) a pattern generating optical element, wherein;

the pattern generating optical element is disposed within the probe outside of the housing, a distance D between an emission point of the semiconductor laser die and an input face of the beam shaping optical element is 50-250 microns, a distance the light travels from exiting the beam shaping optical element to entering the pattern generating optical element is 8-25 mm, and each structured light projector is configured to project a pattern of light onto an intraoral surface when the light source of the structured light projector is activated to emit light through the pattern generating optical element of the structured light projector.

12. An apparatus for intraoral scanning, the apparatus comprising:

an elongate wand comprising a probe at a distal end of the elongate wand; and one or more structured light projectors disposed within the probe, each structured light projector comprising:

(a) a housing;

(b) a light source disposed within the housing and comprising:

a semiconductor laser die; and a beam shaping optical element; and (c) a pattern generating optical element, wherein:

the pattern generating optical element is disposed within the probe outside of the housing such that an angle between an optical axis of the beam shaping optical element and an optical axis of the pattern generating optical element is 50-100 degrees, the apparatus further comprises a mirror disposed within the probe and positioned so as to reflect the light exiting the beam shaping optical element toward the pattern generating optical element, a distance D between an emission point of the semiconductor laser die and an input face of the beam shaping optical element is 50-250 microns, a distance the light travels from exiting the beam shaping optical element to entering the pattern generating optical element is 8-25 mm; and each structured light projector is configured to project a pattern of light onto an intraoral surface when the light source of the structured light projector is activated to emit light through the pattern generating optical element of the structured light projector.

13. The apparatus according to claim 1, wherein for at least one structured light projector of the one or more structured light projectors the semiconductor laser die is a first semiconductor laser die and the light source further comprises a second semiconductor laser die.

14. The apparatus according to claim 13, wherein the first and second semiconductor laser dies have the same wavelength, and wherein the apparatus further comprises a computer processor configured to alternatingly activate the first and second semiconductor laser dies.

15. The apparatus according to claim 1, wherein for at least one of the one or more structured light projectors:

the semiconductor laser die is a first semiconductor laser die and the light source further comprises a second semiconductor laser die, wherein the first and second semiconductor laser dies are mounted within the housing such that the first and second semiconductor laser dies emit laser light in respective first and second directions, the first direction different from the second direction, and the apparatus further comprises a computer processor configured to activate the first and second semiconductor laser dies such that the at least one structured light projector projects a first pattern in the first direction and a second pattern in the second direction.

16. The apparatus according to claim 15, wherein the first and second semiconductor laser dies are mounted on a common submount within the housing.

17. The apparatus according to claim 15, wherein:

the beam shaping optical element is a first beam shaping optical element and the light source further comprises a second beam shaping optical element, the first and second beam shaping optical elements arranged such that laser light from the first semiconductor laser die enters and subsequently exits the first beam shaping optical element and laser light from the second semiconductor laser die enters and subsequently exits the second beam shaping optical element, and the pattern generating optical element is a first pattern generating optical element and the at least one structured light projector further comprises a second pattern generating optical element, the first and second pattern generating optical elements arranged such that the laser light exiting the first beam shaping optical element enters the first pattern generating optical element and the laser light exiting the second beam shaping optical element enters the second pattern generating optical element.

18. An apparatus for intraoral scanning, the apparatus comprising:

an elongate wand comprising a probe at a distal end of the elongate wand;

at least one structured light projector disposed within the probe, each structured light projector comprising:

(a) a housing;

(b) a light source disposed within the housing and comprising:

a first semiconductor laser die;

a second semiconductor laser die, wherein the first and second semiconductor laser dies are mounted within the housing such that the first and second semiconductor laser dies emit laser light in respective first and second directions that are opposite to each other; and a first beam shaping optical element and a second beam shaping optical element; and (c) a first pattern generating optical element and a second pattern generating optical element; and a computer processor configured to activate the first and second semiconductor laser dies such that the at least one structured light projector projects a first pattern of light in the first direction and a second pattern of light in the second direction, wherein:

a distance D between an emission point of the first semiconductor laser die and an input face of the first beam shaping optical element, or between an emission point of the second semiconductor laser die and an input face of the beam shaping optical element, is 50-250 microns, and each structured light projector is configured to project at least one of the first pattern of light or the second pattern of light onto an intraoral surface when the light source of the structured light projector is activated to emit light through at least one of the first pattern generating optical element or the second pattern generating optical element of the structured light projector.

19. The apparatus according to claim 15, wherein the computer processor is configured to activate the first and second semiconductor laser dies such that the at least one structured light projector alternatingly projects the first pattern in the first direction and the second pattern in the second direction.

20. The apparatus according to claim 15, wherein the computer processor is configured to activate the first and second semiconductor laser dies such that the at least one structured light projector projects, at the same time, the first pattern in the first direction and the second pattern in the second direction.

21. An apparatus for intraoral scanning, the apparatus comprising:

an elongate wand comprising a probe at a distal end of the elongate wand; and one or more structured light projectors disposed within the probe, each structured light projector comprising:

(a) a housing;

(b) a light source disposed within the housing and comprising:

a semiconductor laser die; and a beam shaping optical element;

(c) a first pattern generating optical element; and (d) a second pattern generating optical element, wherein:

a distance D between an emission point of the semiconductor laser die and an input face of the beam shaping optical element is 50-250 microns, each structured light projector is configured to project a pattern of light onto an intraoral surface when the light source of the structured light projector is activated to emit light through at least one of the first pattern generating optical element or the second pattern generating optical element of the structured light projector, the first and second pattern generating optical elements are two respective areas on a common substrate that comprises a beam splitter and a reflector disposed within the common substrate, and the apparatus further comprises a computer processor configured to activate the semiconductor laser die such that:

laser light exiting the light source is split by the beam splitter into a first beam and a second beam within the common substrate, and the first beam enters the first pattern generating optical element and the second beam is reflected by the reflector toward the second pattern generating optical element to yield two separate projected patterns that are translationally shifted with respect to each other.

22. The apparatus according to claim 21, wherein the first beam enters the first pattern generating optical element and the second beam is reflected by the reflector toward the second pattern generating optical element to yield two separate projected patterns that are shifted with respect to each other by a distance between optical axes of the first and second pattern generating optical elements.

23. The apparatus according to claim 1, wherein for at least one structured light projector of the one or more structured light projectors the housing is a sealed housing.

24. An apparatus for intraoral scanning, the apparatus comprising:

an elongate wand comprising a probe at a distal end of the elongate wand; and one or more structured light projectors disposed within the probe, each structured light projector comprising:

(a) a housing comprising a transparent window through which light exits the housing;

(b) a light source disposed within the housing and comprising:

a semiconductor laser die; and a beam shaping optical element; and (c) a pattern generating optical element, wherein:

the transparent window comprises the pattern generating optical element, the semiconductor laser die and the beam shaping optical element are disposed within a common chamber of the housing, and each structured light projector is configured to project a pattern of light onto an intraoral surface when the light source of the structured light projector is activated to emit light through the pattern generating optical element of the structured light projector.

* * * * *